US 8,288,111 B2
Oct. 16, 2012

(12) United States Patent
Brate et al.

(54) IMMUNOASSAYS EXHIBITING REDUCED CROSS-REACTIVITY WITH HYDROPHOBIC DRUG ANALYTE METABOLITES

(75) Inventors: Elaine M. Brate, Grayslake, IL (US); David M. Finley, Spring Grove, IL (US); Shelley R. Holets-McCormack, Waukegan, IL (US); David P. Pacenti, Gurnee, IL (US); Ryan E. Piktel, Waukegan, IL (US); Michelle L. Shields, Palos Park, IL (US); Thomas G. Spring, Highland Park, IL (US); Phillip P. Wang, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 184 days.

(21) Appl. No.: 12/126,316

(22) Filed: May 23, 2008

(65) Prior Publication Data

US 2008/0311676 A1 Dec. 18, 2008

Related U.S. Application Data

(60) Provisional application No. 60/940,062, filed on May 24, 2007.

(51) Int. Cl.
*G01N 33/53* (2006.01)

(52) U.S. Cl. ............... 435/7.1; 435/7.2; 435/91; 435/92
(58) Field of Classification Search .................. None
See application file for complete search history.

(56) References Cited

U.S. PATENT DOCUMENTS

| | | | |
|---|---|---|---|
| 5,006,309 A | 4/1991 | Khalil et al. | |
| 5,063,081 A | 11/1991 | Cozzette et al. | |
| 5,089,424 A | 2/1992 | Khalil et al. | |
| 5,135,875 A | 8/1992 | Meucci et al. | |
| 5,169,773 A | 12/1992 | Rosenthaler et al. | |
| 5,239,057 A | 8/1993 | Wang et al. | |
| 5,427,960 A | 6/1995 | Wang et al. | |
| 5,489,668 A | 2/1996 | Morrison et al. | |
| 5,506,114 A | 4/1996 | Sangha | |
| 5,750,413 A | 5/1998 | Morrison et al. | |
| 6,777,198 B2 | 8/2004 | Mendel-Hartvig et al. | |
| 7,091,050 B2 | 8/2006 | Lackie et al. | |
| 7,256,008 B2 | 8/2007 | Spring et al. | |
| 7,592,186 B2 | 9/2009 | Drengler et al. | |
| 7,923,210 B2 | 4/2011 | Drengler et al. | |
| 8,022,188 B2 | 9/2011 | Siegel et al. | |
| 2003/0170881 A1 | 9/2003 | Davis et al. | |
| 2004/0018577 A1 | 1/2004 | Campbell et al. | |
| 2005/0054078 A1 | 3/2005 | Miller et al. | |
| 2006/0160164 A1 | 7/2006 | Miller et al. | |
| 2007/0243631 A1 | 10/2007 | Spring et al. | |
| 2007/0269841 A1 | 11/2007 | Spring et al. | |
| 2008/0020401 A1 | 1/2008 | Grenier et al. | |
| 2008/0160499 A1* | 7/2008 | Grenier et al. .................... 435/4 |

FOREIGN PATENT DOCUMENTS

| | | |
|---|---|---|
| EP | 0 283 801 A2 | 9/1988 |
| EP | 0 314 861 A1 | 5/1989 |
| EP | 0 471 293 A2 | 2/1992 |
| EP | 0 471 293 A3 | 2/1992 |
| EP | 0 487 289 B1 | 5/1992 |
| EP | 473961 B1 | 1/1996 |
| EP | 2174137 B1 | 11/2011 |
| WO | 2007/081868 A1 | 7/2007 |
| WO | 2008/082979 A2 | 7/2008 |
| WO | 2008/082979 A3 | 7/2008 |
| WO | 2008/082982 A2 | 7/2008 |
| WO | 2008/082984 A2 | 7/2008 |
| WO | 2008/082984 A3 | 7/2008 |

OTHER PUBLICATIONS

Abbott Laboratories, Abbott TDx®/TDxFLX®, Product Insert Sheet: Cyclosporine Monoclonal Whole Blood, Ref. 9797-60, Nov. 2005.

Cell Signaling Technology Product Insert Sheet: mTOR antibody [catalog No. 2972 Cell signaling Technology, Beverly, MA], Aug. 27, 2008.

Dade Behiring, Dimension® clinical chemistry system, Product insert sheet, Flex® reagent catridge, CSA., Behring, D.,Ref DF89, Oct. 31, 2002.

Fitzgerald Industries, Monoclonal Antibody Data sheet: Monoclonal mouse anti-cyclosporin A [Catalog No. 10-C66-A, Fitzgerald Industries Intl., Concord, MA], Oct. 23, 2008.

Hytest Data Sheet: Monoclonal mouse anti-FK506 [catalog No. 4FK42, HyTest Ltd., Turku, Finland], May 5, 2010.

Andrew D.J., et al., "Cyclosporin; revisions in monitoring guidelines and review of curent analytical methods", Ann. Clin. Biochem, vol. 39, pp. 424-435, 2002.

Beckman Coulter, Press Realses, "Beckman Coulter Unveils New Cyclosporine Assay for SYNCHRON® Chemistry Immunosuppresant Assay to Meet Increased Demand for Therapeutic Drug", published May 29, 2003.

Beresini MH, et al., "Evaluation of EMIT® Cyclosporine Assay for Use with Whole Blood", Clin. Chem. vol. 39, pp. 2235-2241, 1993.

Dade Behring, Dimension® clinical chemistry system, Product insert sheet, Flex® reagent cartridge, CSA., Behring, D.,RefDF89.

Emeruwa, A.C., "The fluorescent antibody test for the identification of strains of *Clostridium botulinum* type E", Canadian Journal of Microbiology; Dept. of Microbiol., Univ., Winnipeg, Manitoba, Canada, vol. 16, No. 10, p. 917, 1970.

Epps, D.E., et al., "A general, wide-range spectrofluorometric method for measuring the site-specific affinities of drugs toward human serum albumin", Anal. Biochem., vol. 227(2), pp. 342-350, 1995.

(Continued)

*Primary Examiner* — Jacob Cheu
(74) *Attorney, Agent, or Firm* — Audrey L. Bartnicki; Carol L. Larcher; Larcher & Chao Group

(57) ABSTRACT

The present disclosure provides among other things immunoassays exhibiting reduced cross-reactivity with analyte metabolites. Additionally, the present disclosure provides diagnostic immunoassays to determine the concentration or level in a test sample of a hydrophobic drug that metabolizes in vivo or in vitro to form cross-reacting metabolites wherein cross-reactivity with such metabolites of the drug analyte is reduced. In particular, the disclosure provides such immunoassays where the hydrophobic drug is an immunosuppressant drug such as cyclosporine A.

28 Claims, 8 Drawing Sheets

OTHER PUBLICATIONS

Grote, J., "A Practical Method for the Synthesis of a Cyclosporine-Fluorescein Conjugate", Org. Proc. Res. Devel., vol. 9, pp. 822, 2005.
Hänseler, E., et al., "Analyses of the pattern of therapeutic drug monitoring in a University hospital laboratory", Suitability and performance of the CEDIA® assays, Wien Klin. Wochenscher-Suppl., Austria, vol. 191, pp. 23-26, 1992.
Holman, J.W., and Felder, R.A., "Robotic automation of Cyclosporine Analysis in Whole Blood", Clin. Chem., vol. 38, pp. 1440-1443, 1992.
Inamura, N., et al., "Prolongation of Skin Allograft Survival in Rats by a Novel Immunosuppressive Agent, FK506", Transplantation, vol. 45(1), pp. 206-209, 1998.
Jorga A, et al., "Therapeutic Drug Monitoring of Cyclosporine", Transplantation Proc.; vol. 36, (Suppl. 2S); pp. 396S-403S, 2004.
Kahan, et al., "Consensus Document: Hawk's Cay Meeting on Therapeutic Drug Monitoring of cyclosporine", Clin. Chem., vol. 36/8, pp. 1510-1516, 1990.
Mattingly, P.G. and Adamczyk, M., Chemiluminescent N-sulfonylacridinium-9-Carboxamides and their Application in Clinical Assays *Luminescence Biotechnology: Instruments and Applications* (Dyke KV, Ed., CRC Press, Boca Raton, pp. 77-105, 2002.
McBride, J.H., et al., "Measurment of Cyclosporine by Liquid Chromatography and Three Immunoassays from Liver, Cardiac and Renal Transplant Recipients", Clin. Chem., vol. 38, pp. 2300-2306, 1992.
Miller J, et al., "Approaches to minimizing interferences by cross-reacting Molecules in Immunoassays", Clin. Chem, vol. 3, pp. 144-153, 1991.
Mitra, S., "Effects of Temperature, Salt, and pH on Solution Properties", J. Agric. & Food Chem., vol. 45(5), pp. 1587-1595, 1997.
Morris, R.G., "Cyclosporin Assays, Metabolic Cross-Reactivity and Pharmacokinetic Monitoring", Ther. Drug Monit., vol. 22, pp. 160-162, 2000.
Murthy, J.N., et al., "Tacrolimus Metabolite Cross-Reactivity in Different Tacrolimus Assays", Clinical Biochemistry, vol. 31(8), pp. 613-617, 1998.
Oellerich, M., et al., "Therapeutic Drug monitoring of Cyclosporine and Tacrolimus", Clin. Biochem., vol. 31, pp. 309-316, 1998.
Olejnik Y, et al., "Preliminary Evaluation of a New Chemiluminescence Assay (LiaisonCyclosporine; DiaSorin Laboratories) Allowing both C0 and C2 Cyclosporine Levels Determination: Comparison with RIA Method", Transplantation Proc., vol. 37, pp. 172-174, 2005.
Fitzgerald Industries, Monoclonal Antibody Data Sheet: Monoclonal mouse anti-cyclosporin A [Catalog No. 10-C66-A, Fitzgerald Industries Intl., Concord, MA.].
Hytest Data Sheet: Monoclonal mouse anti-FK506 [catalog No. 4FK42, HyTest Ltd., Turku, Finland].
Cell Signaling Technology Product Insert Sheet: mTOR antibody [catalog No. 2972 Cell Signaling Technology, Beverly, MA].
Abbot Laboratories, Abbot TDx®/TDxFLX®, Product Insert Sheet: Cyclosporine Monoclonal Whole Blood, Ref. 9797-60.
Quensalaux, V., et al., "Potential of Monoclonal Antibodies to improve Therapeutic Monitoring of Cyclosporine", Clin. Chem., vol. 33, pp. 32-37, 1987.
Rajkowski, K.M., "Dilution of Biological Samples Increases Cross-Reactant Interference in Immunoassays: A Method for Diagnosing the Origin of Errors in Steroid Enzyme Immunoassay", Gorog, S. (Ed.) Advances in Steroid Analysis '90; $4^{th}$ Symposium of the Analysis on Steroids, Pecs, Hungary, pp. 24-26, Apr. 1990.
Ramsay, C., et al., "Development of an Improved Cyclosporine A (CsA) Immunoassay with no Cross-Reactivity to AM1 and AM9 on the Abbott ARCHITECT® Analyzer", Clin. Chem. Lab. Med., vol. 45 (Special Supplement), M348, 2007.
Schütz E, et al., "Cyclosporine whole blood immunoassays (AxSYM, CEDIA and EMIT®); a critical overview of performance characteristics and comparison with HPLC", Clin. Chem., vol. 44, pp. 2158-2164, 1998.
Simpson, J., "A Specific Method for the Measurment of Cyclosporin A in Human Whole Blood by Liquid Chromatography-Tandem Mass Spectrometry", Therapeutic Drug Monitoring, vol. 20(3), pp. 294-300, 1998.
Soldin SJ, et al., "Lack of Specificity of Cyclosporine Immunoassays Results of a college of American Pathologists Study", Arch Pathol. Lab Med, vol. 127, pp. 19-22, 2003.
Spring, T, et al., "Developemnt of a Low Cross-reactivity Cyclosporine A (CsA) Immunoassay for the Abbott ARCHITECT®", $51^{ST}$ Annual Meeting of the Canadian Society of Clinical Chemists, Toronto, Ontario, Canada, Jun. 9-13, 2007.
Spring, T, et al., "Development of an Improved Cyclospoirine A (CSA) Immunoassay with no Cross-Reactivity on the Abbott ARCHITECT® Analyzer", Clin. Chem., vol. 53(S6), E-56, 2007.
Steimer, W., "Evaluation of the BM CEDIA CSA Assay Compared to HPLC, TDX Monoclonal, AXSYM and EMIT® with both pretreatments", Clinical Chem., vol. 44(6), p. A104, 1998.
Steimer, W., "Performance and Specificity of Monoclonal Immunoassays for Cyclosporine Monitoring: How Specific Is Specific?", Clinical Chemistry vol. 45(3), pp. 371-381, 1999.
Steiner, G., et al, "Determination of Cyclosporine by a Competitive Binding Assay with Cyclophilin", Clin. Chem., vol. 37, pp. 403-410, 1991.
Streit, F., et al., "Rapid Liquid Chromatography-Tandem Mass Spectrometry for Simutlaneous Determination of Sirolimus, Tacrolims and Cyclosporine A in Whole Blood", Clin. Chem., vol. 48, pp. 955-958, 2002.
Terrel, AR, et al., "Evaluation of a No-Pretreatment Cyclosporin A Assay on the Dade Behring Dimension RxL Clinical CHemistry Analyzer", Clin. Chem., vol. 48, pp. 1059-1065, 2002.
Tetin, S.Y. and Hazlett, T.L., Optical Spectroscopy in Studies of Antibody-Hapten Interactions., Methods, vol. 20, pp. 341-361, 2000.
Vining, R.F., "Steriod Radioimmunoassay-Effect of Shortened Incubation Time on Specificity", Clin. Chem., vol. 27, pp. 910-913, 1981.
Wallemacq, P.E., et al., "Evaluation of the New AxSYM Cyclosporine Assay: Comparison with TDx Monoclonal Whole Blood and EMIT® Cyclosporine Assays", Clin. Chem., vol. 45, pp. 432-435, 1999.
Wang P., et al., "A Monoclonal Antibody Fluorescent Polarization Immunoassay for Cyclosporine", Transplantation Proceedings, vol. 22, pp. 1186-1188, 1990.
Wong, P.Y., et al., "Use of $^{125}$I-Labeled Histamine-Cyclosporine C for Monitoring Serum Cyclosporine Concentrations in Transplantation Patients", Clin. Chem., vol. 32, pp. 492-495, 1986.
Yatscoff RW, et al., "Abbott TDx Monoclonal Antibody Assay Evaluated for Measuring Cyclosporine in Whole Blood", Clin. Chem. vol. 36, pp. 1969-1973, 1990.
International Search Report and Written Opinion received for PCT/US2008/064688, mailed Sep. 9, 2008.
Kyne, F., et al., "Abbott TDx 'Selective' Assay Overestimates Cyclosporine in Whole Blood", Clinical Chemistry, 1991, vol. 37, No. 9, pp. 1657-1658.
Moyer, T., et al., "Evaluation of Abbott TDx Monoclonal Assay of Cyclosporine in Whole Blood", Clinical Chemistry, 1991, vol. 37, No. 8, pp. 1120-1121.
Wang, P., et al., "Cyclosporine Monitoring by Fluorescence Polarization Immunoassay", Clinical Biochemistry, 1991, vol. 24, pp. 55-58.

\* cited by examiner sirolimus

RAD

IMMUNOASSAYS EXHIBITING REDUCED CROSS-REACTIVITY WITH HYDROPHOBIC DRUG ANALYTE METABOLITES

RELATED APPLICATION INFORMATION

This application claims the priority of U.S. Provisional Patent Application Ser. No. 60/940,062 filed on May 24, 2007, the contents of which are herein incorporated by reference.

TECHNICAL FIELD

The present disclosure relates to immunoassays exhibiting reduced cross-reactivity with analyte metabolites. Among other things, the disclosure relates to diagnostic immunoassays to determine the concentration or level in a test sample of a hydrophobic drug that metabolizes in vivo or in vitro to form cross-reacting metabolites wherein cross-reactivity with such metabolites of the drug analyte is reduced. In particular, the disclosure relates to such immunoassays where the hydrophobic drug is an immunosuppressant.

BACKGROUND

Immunosuppressant drugs such as sirolimus (also known as rapamycin), tacrolimus (also known as FK506), and cyclosporine ("CsA") are effective for the treatment of organ or tissue rejection following transplant surgery, of graft versus host disease and of autoimmune diseases in humans. During immunosuppressant drug therapy, monitoring the blood concentration levels of the immunosuppressant is an important aspect of clinical care because insufficient drug levels lead to graft (organ or tissue) rejection and excessive levels lead to undesired side effects and toxicities. For instance, tacrolimus exhibits some toxicity similar to that of CsA, which includes nephrotoxicity, gastrointestinal tract complications and neurotoxicity. (See, Murthy, J. N., et al., *Clinical Biochemistry*, 31(8):613-617 (1998)). Blood levels of immunosuppressants are therefore measured so drug dosages can be adjusted to maintain the drug level at the appropriate concentration. Diagnostic assays for determination of immunosuppressant blood levels have thus found wide clinical use.

Tacrolimus is the generic name for a macrolide immunosuppressant produced by the bacterium *Streptomyces tsukabaensis*, in the soil (See, Inamura, N., et al., *Transplantation*, 45(1):206-209 (1988)). Tacrolimus has been used intravenously and orally for the prevention of organ rejection, particularly in patients receiving liver, kidney or bone marrow transplantation.

Cyclosporine is an immunosuppressive drug obtained from soil fungus (*Tolypocladium inflatum*). While primarily used to prevent organ rejection after transplant, CsA also has been used to treat other illnesses, such as aplastic anemia, or to prevent graft versus host disease. CsA's mode of action is to block T cell activation by preventing transcription of the IL-2 gene.

Tacrolimus has an in vivo potency 50-100 times greater than cyclosporine CsA (See, Murthy, J. N., et al., supra (1998)). The immunosuppressive effect of tacrolimus is similar to CsA and is thought to be through the selective inhibition of the generation of cytotoxic T cells. Id.

Other immunosuppressive drugs include sirolimus, everolimus, temsorolimus, zotarolimus, and mycophophenolic acid.

The primary target of sirolimus, everolimus (RAD-001), temsorolimus and zotarolimus is mTOR (mammalian Target of Rapamycin), a specific cell-cycle regulatory protein, the inhibition of which leads to suppression of cytokine-driven T-lymphocyte proliferation. Everolimus is used as an immunosuppressant to prevent rejection of organ transplants and as a cancer-suppressing drug. The contra-indication in the use of everolimus is a certain rise in cholesterol levels and therefore an increased cardio-vascular risk.

Mycophenolate mofetil (MMF) is an ester derivative of mycophenolic acid (MPA) and is approved as an immunosuppressant drug in renal transplant patients. The prodrug MMF is rapidly transformed in vivo to the active immunosuppressant MPA, which inhibits inosine monophosphate dehydrogenase 2. MMD thus suppresses the de novo synthesis of guanosine nucleotides, especially in T and B lymphocytes, and stops their proliferation.

A variety of different diagnostic immunoassays are commercially available for monitoring the blood concentrations of immunosuppressive drugs. While the immunoassays are available in a variety of formats, all use the binding of an antibody or binding protein (e.g. FKBP) to the immunosuppressant drug. A commonly-used prior art immunoassay is an assay which involves the binding of a first antibody to the immunosuppressant drug and the binding of labeled immunosuppressant (e.g., acridinylated sirolimus or tacrolimus) to the remaining free antibody binding sites, followed by quantitation through detection of the acridinium label.

Several of these immunoassays use organic solvents to extract the tacrolimus from whole blood samples. The organic solvent increases the equilibrium dissociation constant ($K_D$) and/or lowers the functional activity of the antibody used in the assays. The reduced activity of the antibody leads to lower assay sensitivity and potentially lowers accuracy and robustness. Thus, the effectiveness of these immunoassays is affected by the particular extraction and denaturating solvent for the immunosuppressant that is used.

Likewise, the generation in vivo of metabolites to the immunosuppressive drug can impact assay results. Current literature suggests that the generation of CsA metabolites M17 (also known as AM1) and M1 (also known as AM9) can mask the concentration of active parent drug (CsA). Tacrolimus and sirolimus are known to form metabolites in vivo. The first generation major metabolites of tacrolimus are 13-O-demethylated tacrolimus ("M-I"), 31-O-demethylated tacrolimus ("M-II"), and 15-O-demethylated tacrolimus ("M-III").

Immunoassay for the determination of MPA in serum (e.g., following MMF treatment) yields results that are higher than those obtained with the HPLC methods. This is believed due to the cross-reactivity of MPA metabolites with the monoclonal antibodies. MPA is metabolized mainly to a glucuronide derivative (MPAG), which is believed inactive. Recently, two other metabolites of MPA have been identified, including the acyl glucuronide of MPA.

Needless to say, the appropriate dosage of the immunosuppressant drug is critical for organ transplantation patients and needs to be accurately and reproducibly measured in the presence of metabolites.

Therefore, there is a need in the art for new immunoassays that provide accurate measures of drug analytes, e.g., immunosuppressives in the presence of their cross-reacting metabolites. It is an object of the disclosure to provide such immunoassays. It is a further object to provide such immunoassays which optimally avoid the problems that accompany modification of the extraction reagent composition to engender reduced cross-reactivity with metabolites. It is yet another object to provide immunoassays which optimally avoid the cost and labor considerations that accompany selection of an antibody or antibody optimization for reduced cross-reactivity with cross-reacting drug metabolites. Additional objects and embodiments will be apparent from the description herein.

SUMMARY

In one embodiment, the disclosure relates to an immunoassay for assessing the amount of an analyte of interest in a test sample, wherein the analyte is a hydrophobic drug that metabolizes to form one or more cross-reacting metabolites, wherein the immunoassay has less than about 10% cross-reactivity (optionally, less than about 5% cross-reactivity) with any one or more cross-reacting metabolites present in the sample. The test sample can be a variety of patient samples, including whole blood.

The hydrophobic drug is one that is soluble in detergent or organic solvent. In one embodiment, the hydrophobic drug is an immunosuppressive, especially an immunosuppressive is selected from the group consisting of tacrolimus, sirolimus and cyclosporine. In one aspect, the immunosuppressive is tacrolimus and the metabolite is selected from the group consisting of M-I, M-II, M-III, and combinations thereof. In another aspect, the immunosuppressive is cyclosporine and the metabolite is selected from the group consisting of M1 (also known as AM9), M8, M9, M13, M17 (also known as AM1), M18, M21 and combinations thereof. In still another aspect, the immunosuppressive is cyclosporine and the metabolites are AM1 and AM9. In yet another aspect, the immunosuppressive is sirolimus and the metabolite is selected from the group consisting of 11-Hydroxy-sirolimus, 41-O-demethyl-sirolimus, 7-O-demethyl-sirolimus, and/or 41-O-demethyl-hydroxy-sirolimus and combinations thereof.

In one embodiment, the immunoassay comprises the steps of:

(a) contacting the test sample with one or more pretreatment reagents to form a first mixture, wherein the one or more pretreatment reagents lyse any cells and solubilize any analyte present in the test sample;

(b) contacting the first mixture with an antibody specific for the analyte to form a second mixture comprising a complex of the antibody with analyte or metabolite;

(c) washing the second mixture to remove any analyte and any metabolite not complexed with the antibody and to form a third mixture in which the analyte concentration is decreased to near the equilibrium dissociation constant ($K_D$) of the antibody for analyte;

(d) contacting the third mixture with a specific binding partner of the antibody labeled with a detectable label ("tracer") to form a fourth mixture comprising an complex of the antibody with tracer ("antibody-tracer complex");

(e) washing the fourth mixture to remove any tracer not complexed with antibody; and (f) detecting the antibody-tracer complex as measure of the amount of analyte present in the sample. In one embodiment, the antibody specific for the analyte in step (b) is attached to a solid phase.

In one aspect of such an immunoassay, the one or more pretreatment reagents precipitate in step (a) any analyte binding protein present in the sample. Optionally the assay further comprises removing any analyte binding protein from the first mixture. The one or more pretreatment reagents can be selected from a variety of different pretreatment reagents, including in one aspect one or more pretreatment reagents that comprise saponin, methanol and zinc sulfate. In another aspect, the one or more pretreatment reagent comprises saponin (e.g., optionally present in a first pretreatment reagent), in combination with methanol, ethylene glycol and zinc sulfate (e.g., optionally present in a second pretreatment reagent).

In another aspect of such an immunoassay, optionally the antibody specific for the analyte is immobilized on a solid phase. The antibody can be selected from a variety of different antibodies. In one aspect, an antibody can be selected from the group consisting of a polyclonal antibody, a monoclonal antibody, a humanized antibody, a F(ab)'$_2$, a chimeric antibody, a human antibody, and an affinity maturated antibody. The solid phase can be a variety of different solid phases, including in one aspect a solid phase selected from the group consisting of a magnetic particle, bead, test tube, microtiter plate, cuvette, membrane, a scaffolding molecule, film, filter paper, disc, and chip.

In still another aspect of such an immunoassay, the detectable label employed for the tracer can be a variety of different detectable labels, including in one aspect wherein the detectable label is selected from the group consisting of a radioactive label, an enzymatic label, a chemiluminescent label, a fluorescent label, a thermometric label, and an immuno-polymerase chain reaction label. Optionally the tracer can comprise multiple binding partners.

In such an immunoassay, in one embodiment the second mixture further comprises an assay diluent. Optionally the assay diluent comprises a buffer, salt, detergent, or combinations thereof. Further, optionally the assay diluent comprises a buffer, salt, detergent, solvent, or combinations thereof. In another embodiment the fourth mixture in step (d) further comprises a detergent. Optionally the detergent is Triton® X-100, either in aromatic or chemically reduced form. In one embodiment, the Triton® X-100 is reduced Triton® X-100.

In one aspect of such an immunoassay, the antibody in step (b) has a $K_D$ for cross-reacting metabolite that is between about 10-fold and about 1000-fold higher than for analyte.

In a further aspect of such an immunoassay, the amount of antibody in step (b) is from between about 0.1% and about 10% of the amount of analyte in the test sample. Additionally, in a still further aspect, the analyte and metabolite concentrations are decreased in the third mixture in step (c) by from about 10-fold to about 500-fold as compared to in the test sample. Moreover, in another aspect, in step (d) the amount of analyte present in a complex with antibody ranges from about 1.0 and about 10.0 nM, and the tracer is present in an amount from between about 0.1 to about 1.0 nM.

In yet another aspect of such an immunoassay, optionally the immunoassay further comprises: (i) incubating the first mixture in step (a) for a first incubation period; (ii) incubating the second mixture in step (b) for a second incubation period; and (iii) incubating the fourth mixture in step (d) for a third incubation period. The first incubation period optionally comprises a period of from about 2 minutes to about 60 minutes. The second incubation period optionally comprises a period of from about 2 minutes to about 30 minutes. The third incubation period optionally comprises a period of from about 2 minutes to about 30 minutes.

In yet a further aspect of such an immunoassay, optionally the immunoassay relates an amount of the antibody-tracer complex formed to the amount of the analyte in the test sample either by use of a standard curve for the analyte, or by comparison to a reference standard.

DETAILED DESCRIPTION

Figure 1:
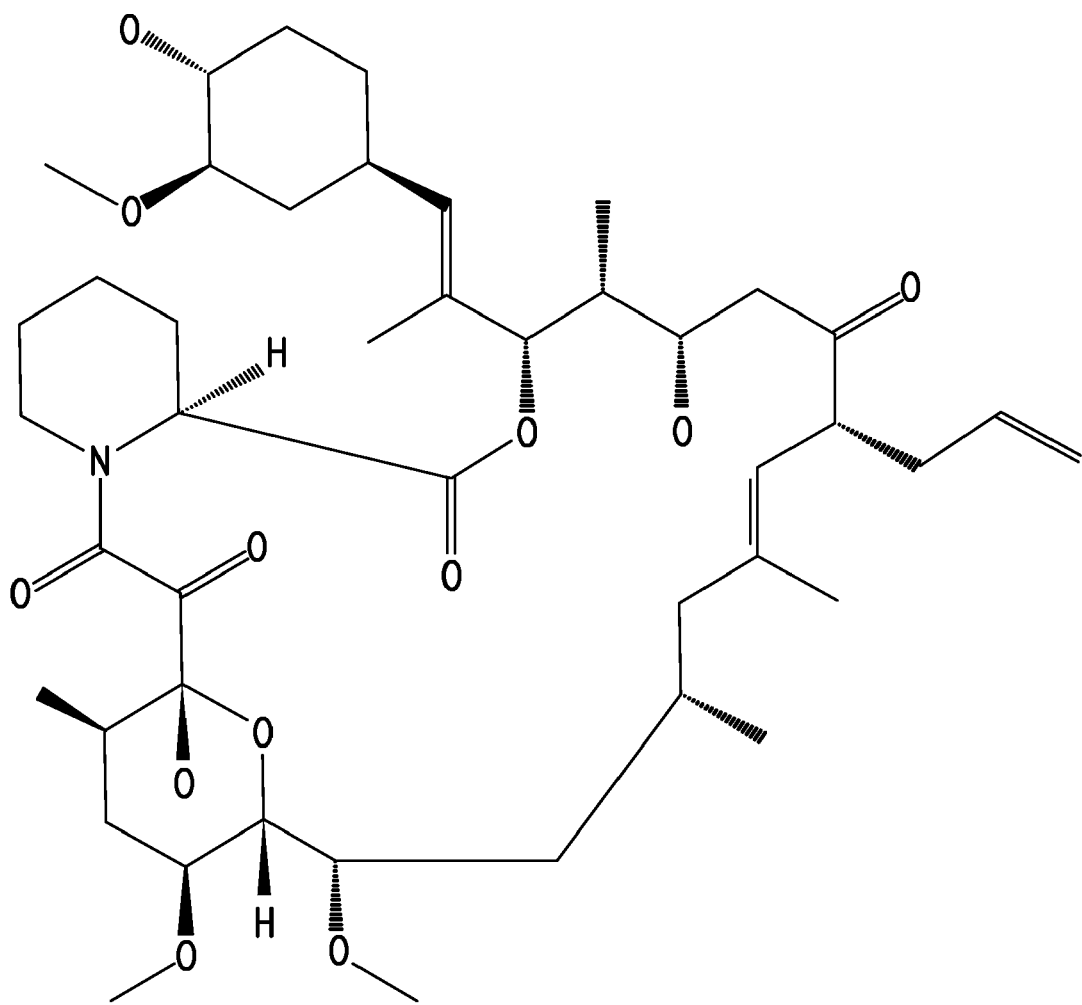
FIG. 1 shows the structure of tacrolimus.
Figure 2:
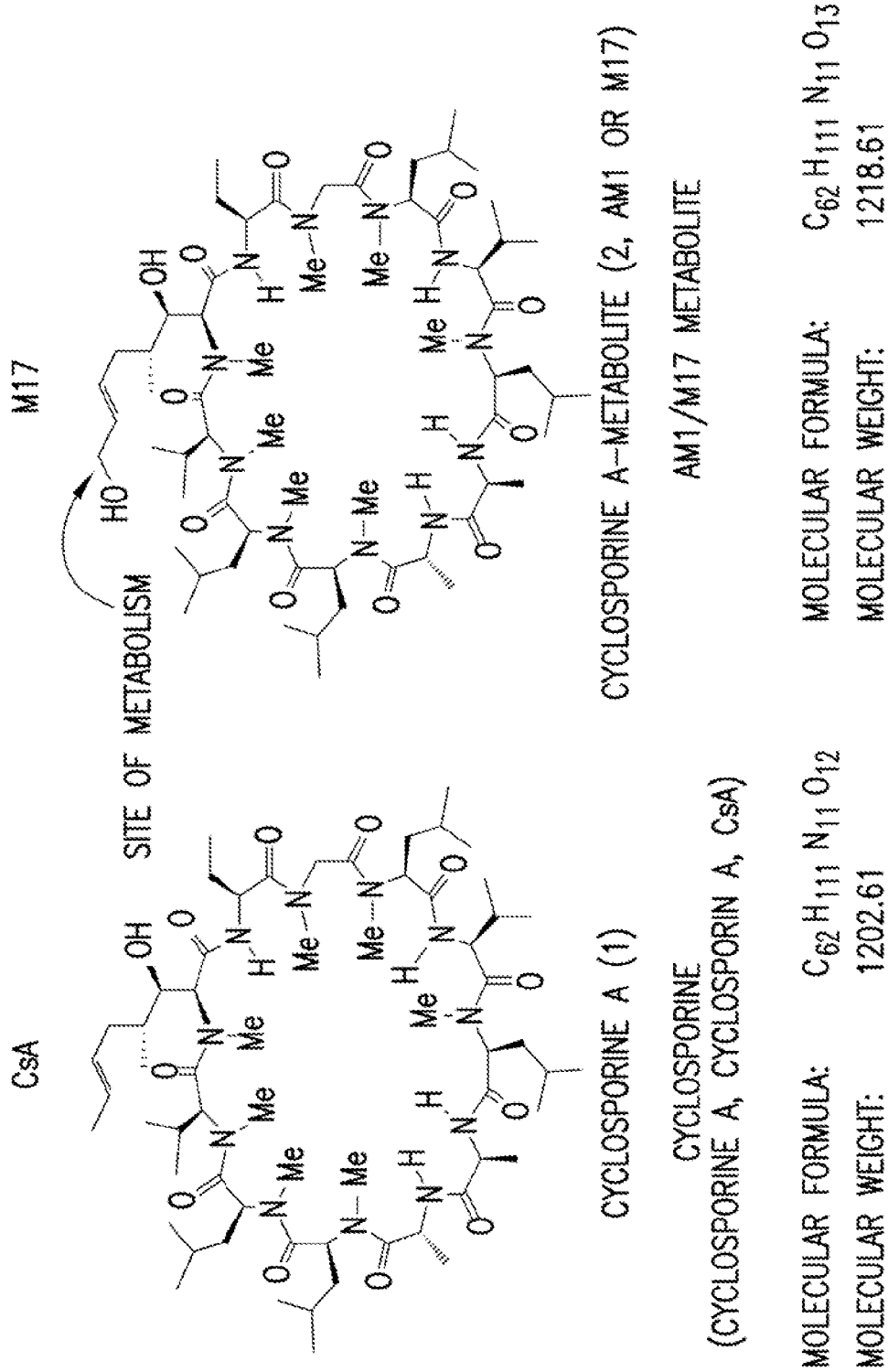
FIG. 2 shows the structure of cyclosporine A ("CsA" on the left) and a metabolite of CsA (on the right), which is referred to herein as "AM1 or M17". The molecular formula and molecular weight of CsA and metabolite M17 (AM1) are listed below the corresponding structure.
Figure 3A:
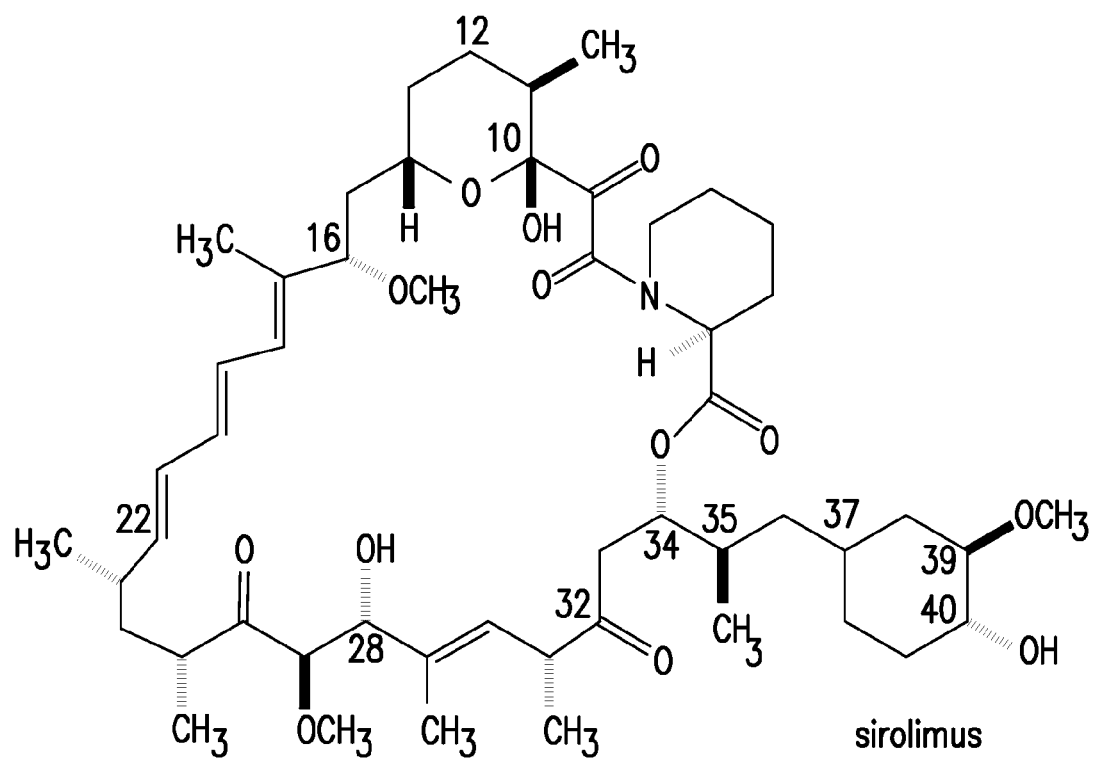
FIGS. 3A and 3B shows the structure of sirolimus (FIG. 3A) and the structural difference of everolimus (RAD) from sirolimus (FIG. 3B).
Figure 3B:
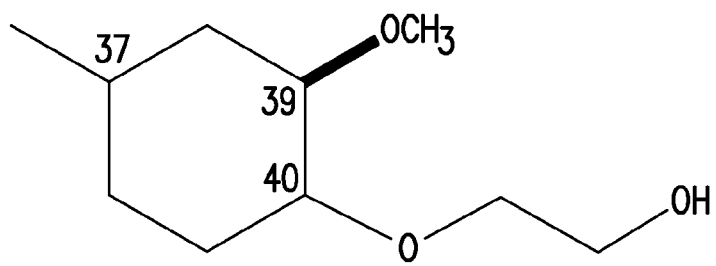

The present disclosure provides immunoassays exhibiting reduced cross-reactivity with analyte metabolites where the analyte is a hydrophobic drug that metabolizes in vivo or in vitro. In particular, the disclosure provides diagnostic immunoassays to determine the concentration or level of a hydrophobic drug in a test sample wherein cross-reactivity with metabolites of the analyte drug is reduced. In one embodiment the hydrophobic drug is an immunosuppressant.

I. Definitions a. Hydrophobic drug that metabolizes in vivo or in vitro. As used herein, a "hydrophobic drug" is one that has a thermodynamic tendency to reduce the surface area of the drug molecule exposed to water, resulting in low solubility in aqueous solutions, e.g., a poorly water-soluble or water-insoluble drug. Hydrophobic drugs are described in the various pharmacopeias such as United States Pharmacopeia (U.S.P.), other country pharmacopeias, and other medical works. Solubility can be assessed by various means well known in the art, e.g., the partition coefficient between water or buffer and n-octanol or cyclohexane. A "hydrophobic drug that metabolizes in vivo or in vitro" is a hydrophobic drug that, through biochemical modification or degradation (e.g., through specialized enzymatic systems), is converted to another compound, typically a lipophilic chemical compound that is more readily excreted as a polar product. The present disclosure concerns only those hydrophobic drugs that metabolize to form cross-reacting metabolites (as described herein). Examples include immunosuppressives as well as steroid drugs (e.g., prednisone, prednisolone, cortisone, and the like).

b. Immunosuppressive. As used herein, the term "immunosuppressive drug," "immunosuppressive agent" or "immunosuppressant" refers to a drug that slows or halts immune system activity in a subject. Immunosuppressive agents can be given to a subject to prevent the subject's immune system from mounting an immune response after an organ transplant or for treating a disease that is caused by an overactive immune system. Examples of immunosuppressive agents include, but are not limited to, a calcineurin inhibitor, such as, but not limited to, cyclosporine, tacrolimus, a target of rapamycin (mTOR), such as, but not limited to, sirolimus, everolimus, zotarolimus, or temsorolimus, or an inhibitor of inosine monophosphate dehydrogenase, such as mycophenolate mofetil, an inhibitor of dihydrofolic acid reductase, such as, but not limited to, methotrexate, a corticosteroid, such as, but not limited to, prednisolone and methylprednisolone, or an immunosuppressive antimetabolite, such as, but not limited to, azathioprine.

c. Antibody. As used herein, the terms "antibody" and "antibodies" refer to monoclonal antibodies, multispecific antibodies, human antibodies, humanized antibodies (fully or partially humanized), animal antibodies such as, but not limited to a bird (for example, a duck or goose), a shark or whale, a mammal, including a non-primate (for example, a cow, pig, camel, llama, horse, goat, rabbit, sheep, hamsters, guinea pig, cat, dog, rat, mouse, etc) or a non-human primate (for example, a monkey, such as a cynomologous monkey, a chimpanzee, etc), recombinant antibodies, humanized antibodies, chimeric antibodies, single-chain Fvs ("scFv"), single chain antibodies, single domain antibodies, Fab fragments, F(ab') fragments including F(ab)'2, disulfide-linked Fvs ("sdFv"), and anti-idiotypic ("anti-Id") antibodies (including, for example, anti-Id antibodies to antibodies of the present disclosure), and functionally active epitope-binding fragments of any of the above. In particular, antibodies include immunoglobulin molecules and immunologically active fragments of immunoglobulin molecules, namely, molecules that contain an antigen binding site. Immunoglobulin molecules can be of any type (for example, IgG, IgE, IgM, IgD, IgA and IgY), class (for example, $IgG_1$, $IgG_2$, $IgG_3$, $IgG_4$, $IgA_1$ and $IgA_2$) or subclass.

As used herein, the term "humanized" antibody refers to an immunoglobulin variant or fragment thereof, which is capable of binding to a predetermined antigen and which comprises framework regions having substantially the amino acid sequence of a human immunoglobulin and CDRs having substantially the amino acid sequence of a non-human immunoglobulin. Ordinarily, a humanized antibody has one or more amino acid residues introduced into it from a source that is non-human. In general, the humanized antibody will include substantially all of at least one, and typically two, variable domains (such as, Fab, Fab', $F(ab')_2$, Fabc, Fv) in which all or substantially all of the CDR regions correspond to those of a non-human immunoglobulin and all or substantially all of the framework ("FR") regions are those of a human immunoglobulin consensus sequence. The humanized antibody optimally comprises at least a portion of an immunoglobulin constant region ("Fc"), typically that of a human immunoglobulin. Generally, the antibody will contain both the light chain as well as at least the variable domain of a heavy chain. The humanized antibody can be selected from any class of immunoglobulins, including IgM, IgG, IgD, IgA and IgE, and any isotype, including $IgG_1$, $IgG_2$, $IgG_3$ and $IgG_4$. The humanized antibody may comprise sequences from more than one class or isotype, and selecting particular constant domains to optimize desired effector functions is within those skilled in the art.

d. Capture antibody. An antibody employed for capture (e.g., separation) of an analyte from sample in an immunoassay is referred to as a "capture antibody". A capture antibody as described herein includes an antibody that is a specific binding partner of an analyte (e.g., a hydrophobic drug such as an immunosuppressive).

e. Specificity. As used herein, "specific" or "specificity" in the context of an interaction between members of a specific binding pair (as defined herein, e.g., an antigen and antibody) refers to the selective reactivity of the interaction. As an example, the phrase "specific for an analyte" and analogous terms thereof refer to peptides, polypeptides, proteins, fusion proteins and antibodies that specifically bind to an analyte such as an immunosuppressive agent (including but not limited to, tacrolimus, sirolimus, everolimus and CsA) and that do not specifically bind to other binding competitors (such as, but not limited to, metabolites, peptides, polypeptides, proteins, agents or drugs). A peptide, polypeptide, protein, or antibody that specifically binds to an immunosuppressive agent may bind to other metabolites, peptides, polypeptides, proteins, agents or drugs with lower binding affinity as determined by, for example, diagnostic immunoassays, BIAcore®, KinExA® or other assays known in the art. Antibodies or antibody fragments that immunospecifically bind to an immunosuppressive agent can be identified, for example, by diagnostic immunoassays, BIAcore®, KinExA® or other techniques known to those of skill in the art. An antibody binds immunospecifically to an immunosuppressive agent with a higher binding affinity than to any cross-reactive antigen as determined using experimental techniques, such as, but not limited to, radioimmunoassays ("RIA") and enzyme-linked immunosorbent assays ("ELISAs") (See, for example, Paul, ed., *Fundamental Immunology*, 2nd ed., Raven Press, New York, pages 332-336 (1989)).

f. Binding constants (e.g., $K_D$, $k_a$, and $k_d$). As used herein, the term "equilibrium dissociation constant" or "$K_D$" as used interchangeably, herein, refers to the value obtained by dividing the disassociation rate constant ($k_{off}$) by the association rate constant ($k_{on}$). The association rate constant, the disassociation rate constant and the equilibrium dissociation constant are used to represent the binding affinity of an antibody to an antigen.

The term "association rate constant", "$k_{on}$" or "$k_a$" as used interchangeably herein, refers to the value indicating the binding rate of an antibody to its target antigen or the rate of complex formation between an antibody and antigen as shown by the equation below:

Antibody("*Ab*")+Antigen("*Ag*")→*Ab–Ag*.

Methods for determining association rate constants are well known in the art. For example, a BIAcore® (Sweden) assay can be used. Additionally, a KinExA® (Kinetic Exclusion Assay) assay, available from Sapidyne Instruments (Boise, Id.) can also be used.

The term "disassociation rate constant", "$k_{off}$" or "$k_d$" as used interchangeably herein, refers to the value indicating the disassociation rate of an antibody from its target antigen or separation of Ab-Ag complex over time into free Ab and antigen as shown by the equation below:

*Ab*+*Ag*←*Ab–Ag*.

Methods for determining disassociation rate constants are well known in the art. For example, a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

g. Binding Competitor (e.g., Cross-Reacting Metabolite). As used herein, the term "binding competitor" refers to any molecule that competes or cross-reacts with a molecule containing an epitope of interest and thus precludes the molecule from interacting or binding with its specific binding partner. Preferably, the molecule that competes or cross-reacts with the molecule containing the epitope of interest binds to the specific binding partner with a lower affinity (such as, but not limited to, a higher $K_D$, a higher $k_d$ or a lower $k_a$) than the molecule containing the epitope of interest. Examples of a metabolite binding competitor include, for example, metabolites of drugs, including but not limited to metabolites of immunosuppressive agents: such as 13-O-demethylated tacrolimus ("M-I"), 31-O-demethylated tacrolimus ("M-II") and 15-O-demethylated tacrolimus ("M-III"), which are metabolites of tacrolimus; or M1, M8, M9, M13 M17, M18 or M21, which are the metabolites of cyclosporine. CsA and its metabolites are described in detail in the literature (e.g., in Kahan et al., "Consensus Document: Hawk's Cay Meeting on Therapeutic Drug Monitoring of Cyclosporine," *Clin. Chem.*, 36/8:1510-1516 (1990), which is herein incorporated by reference for its teachings regarding metabolites). For example, cyclosporine antibody has $K_D$ for parent cyclosporine drug of $9.5 \times 10^{-10}$ M and $K_D$ for metabolite M17 of $1.45 \times 10^{-8}$ M. Binding competitors also can include: haptens; hormones; drugs; enzymes; receptors; proteins; peptides; polypeptides; oligonucleotides; or polynucleotides.

h. Cross-reactivity. As used herein, the terms "cross-reacts" or "cross-reactivity" refers to the ability of two epitopes, molecules or ligands to react with the same site on the same specific binding partner, typically with different affinities.

i. Epitope. As used herein, the term "epitope", "epitopes" or "epitopes of interest" refer to a site(s) on any molecule that is recognized and is capable of binding to a complementary site(s) on its specific binding partner. The molecule and specific binding partner are part of a specific binding pair. For example, an epitope can be a polypeptide, protein, hapten, carbohydrate antigen (such as, but not limited to, glycolipids, glycoproteins or lipopolysaccharides) or polysaccharide and its specific binding partner, can be, but is not limited to, an antibody.

j. Buffer. Examples of buffers that can be used, include, but are not limited to, 2-(N-morpholino)ethanesulfonic acid ["MES"], 3-(N-morpholino)propanesulfonic acid ["MOPS"], (4-(2-hydroxyethyl)-1-piperazineethanesulfonic acid) ["HEPES"], 2-amino-2-hydroxymethyl-1,3-propanediol[trishydroxymethylaminomethane or "TRIS"], phosphate, citrate, borate buffers or combinations thereof. In one embodiment, MES is a preferred buffer.

k. Salt. Examples of salts that can be used are sodium chloride, potassium chloride, zinc sulfate or combinations thereof. A preferred salt is sodium chloride.

l. Protein. Examples of proteins that can be used are bovine serum albumin ("BSA"), fish gelatin, bovine gamma globulin, or combinations thereof. A preferred protein is bovine gamma globulin.

m. Solvents. Examples of solvents that can be used are organic solvents. Examples of organic solvents that can be used include, but are not limited to, dimethylformamide, dimethyl sulfoxide, propylene glycol, ethylene glycol, methanol, ethanol or combinations thereof. Preferred solvents are methanol and ethylene glycol.

n. Assay diluent. As used herein, the term "assay diluent" refers to any liquid or solid material that can be employed for the reaction conditions of a diagnostic immunoassay. The composition of the assay diluent will vary depending on how the assay diluent is to be used (e.g., can be further optimized for different hydrophobic drug assays). For example, an assay diluent can comprise at least one buffer, optionally at least one salt, optionally at least one detergent, and/or optionally at least one solvent (e.g., water). In some embodiments, the assay diluent further comprises one or more liquid or solid organic additive, e.g., including but not limited to methanol, ethylene glycol or propylene glycol, or detergent. Moreover, an assay diluent may comprise any combination of at least one buffer, optionally at least one salt, optionally at least one detergent, and optionally at least one solvent. By way of another example, an assay diluent can comprise buffer having a pH from about 5 to about 8 (e.g., MES buffer) and salt having a concentration from about 1 M to about 4.5 M (e.g., especially about 1.9 M NaCl, or about 4.5 M NaCl). The assay diluent can be used from a commercially marketed assay, e.g., an assay for ARCHITECT®, TDx or AxSYM® analyzer (Abbott Laboratories, Abbott Park, Ill.). Typically assay diluents are customized for each assay.

o. Pretreatment Reagents (e.g., Lysis, Precipitation and/or Solubilization reagents). Pretreatment reagents used in a diagnostic assay as described herein are those that lyse any cells and solubilize any analyte that are present in a test sample. Among other things, solubilizing the analyte entails release of the analyte from any endogenous binding proteins ("analyte binding proteins") present in the sample. Generally, one or more pretreatment reagents can be used, e.g., a single pretreatment reagent can be used alone, or a first pretreatment reagent can be used with a second, or third, etc. other pretreatment reagents. A pretreatment reagent, e.g., use of one or more pretreatment reagents, may be homogeneous (not requiring a separation step) or heterogeneous (requiring a separation step). With use of a heterogeneous pretreatment reagent there is additional removal of any analyte binding proteins from the test sample prior to proceeding to the next step of the assay. The pretreatment reagents can comprise: (a) one or more solvents and salt, (b) one or more solvents, salt and detergent, (c) detergent, or (d) detergent and salt.

p. Wash buffer. Wash buffer is employed for assay washing steps and refers to commercially available ARCHITECT® Wash Buffer (Abbott Laboratories, Abbott Park, Ill.), although another wash buffer (e.g., buffered saline with a small amount of detergent) also optionally can be employed.

q. Detergents. Examples of detergents that can be used include, but are not limited to, anionic detergents, cationic detergents, non-ionic detergents or zwitterionic detergents. An assay diluent containing one or more detergents can be used to stabilize and/or solubilize proteins or other analytes of interest contained within a sample, such as a test sample, to prevent nonspecific binding during the course of a diagnostic immunoassay, to rupture cells contained within a sample, etc. Anionic detergents include, but are not limited to, chenodeoxycholic acid, chenodeoxycholic acid sodium salt, cholic acid, dehydrocholic acid, digitonin, digitoxigenin, N,N-dimethyldodecylamine N-oxide, docusate sodium salt, glycochenodeoxycholic acid sodium salt, glycocholic acid hydrate, glycocholic acid sodium salt hydrate, glycodeoxycholic acid monohydrate, glycolithocholic acid 3-sulfate disodium salt, glycolithocholic acid ethyl ester, N-lauroylsarcosine sodium salt, N-lauroylsarcosine solution, lithium dodecyl sulfate, lugol solution, 1-octanesulfonic acid sodium salt, sodium 1-butanesulfonate, sodium 1-decanesulfonate, sodium 1-dodecanesulfonate, sodium 1-heptanesulfonate anhydrous, sodium 1-nonanesulfonate, sodium 1-propanesulfonate monohydrate, sodium 2-bromoethanesulfonate, sodium cholate hydrate, sodium choleate, sodium deoxycholate, sodium deoxycholate monohydrate, sodium dodecyl sulfate, sodium hexane sulfonate anhydrous, sodium octyl sulfate, sodium pentanesulfonate anhydrous, sodium taurocholate, taurochenodeoxycholic acid sodium salt, taurodeoxycholic acid sodium salt monohydrate, taurodeoxycholic acid sodium salt hydrate, taurolithocholic acid 3-sulfate disodium salt, taurursodeoxycholic acid sodium salt, ursodeoxycholic acid or combinations thereof, all available from Sigma-Aldrich, St. Louis, Mich.

Cationic detergents include, but are not limited to, alkyltrimethylammonium bromide, benzalkonium chloride, benzyldimethylhexadecylammonium chloride, benzyldimethylhexadecylammonium bromide, benzyltrimethylammonium tetrachloroiodate, dimethyldioctadecylammonium bromide, dodecylethyldimethylammonium bromide, dodecyltrimethylammonium bromide, ethylhexadecyldimethylammonium bromide, Girard's reagent T, hexadecyltrimethylammonium bromide or combinations thereof, all available from Sigma-Aldrich, St. Louis, Mich.

Non-ionic detergents, include, but are not limited to, Big-CHAP, bis(polyethylene glycol bis[imidazoyl carbonyl]), Brij®35, Brij®56, Brij®72, Cremophor® EL, decaethylene glycol monododecyl ether, N-decanoyl-N-methylglucamine, n-decyl α-D-maltoside, n-dodecyl β-D-maltoside, heptaethylene glycol monodecyl ether, hexaethylene glycol monododecyl ether, octaethylene glycol monodecyl ether, octaethylene glycol monododecyl ether, octaethylene glycol monohexadecyl ether, octaethylene glycol monooctadecyl ether, octaethylene glycol monotetradecyl ether, pentaethylene glycol monodecyl ether, pentaethylene glycol monododecyl ether, pentaethylene glycol monohexadecyl ether, pentaethylene glycol monohexyl ether, pentaethylene glycol monooctadecyl ether, polyethylene glycol diglycidyl ether, polyethylene glycol ether W-1, polyoxyethylene 10 tridecyl ether, polyoxyethylene 100 stearate, polyoxyethylene 20 isohexadecyl ether, saponin, Span®20, Span®40, Span®60, Span®65, Span®80, Span®85, Tergitol, Triton® CF-21, Triton® CF-32, Triton® DF-12, Triton® DF-16, Triton® GR-5M, Triton® QS-15, Triton® QS-44, Triton® X-15, Triton®X-100, Triton® X-102, Triton® X-114, TWEEN®20, TWEEN®21, TWEEN®40, TWEEN®60, TWEEN®61, TWEEN®65, TWEEN®80, TWEEN®81, TWEEN®85 or combinations thereof, all available from Sigma-Aldrich, St. Louis, Mich.

Zwitterionic detergents include, but are not limited to, CHAPS, 3-(Decyldimethylammonio)propanesulfonate inner salt, (Dodecyldimethylammonio)propanesulfonate inner salt, 3-(N,N-Dimethylmyristylammonio)propanesulfonate, 3-(N,N-Dimethyloctadecylammonio)propanesulfonate, 3-(N,N-dimethyloctylammonio)propsanesulfonate inner salt, 3-(N,N-dimethylpalmitylammonio)proposanesulfonate or combinations thereof, all available from Sigma-Aldrich, St. Louis, Mich.

A preferred detergent is Triton® X-100, either with the standard aromatic ring, or with the chemically-reduced aliphatic ring in the hydrophobic region of the detergent ("reduced form").

r. Specific binding pair/partner. As used herein, the term "specific binding partner" means a member of a specific binding pair. The members of a specific binding pair comprise at least two molecules each of which have at least one structure complementary to a structure of the other molecule, where the at least two molecules are able to bind through a binding of the complementary structures. The term also includes molecule complexes such as, for example, enzymes consisting of Apo enzyme and coenzyme, proteins consisting of a plurality of subunits, lipoproteins consisting of protein and lipids, etc. Specific binding partners may be substances which occur naturally or else have been prepared for example by chemical synthesis, microbiological techniques and/or methods of genetic manipulation. Examples of specific binding partners, include but are not limited to, antibodies, antigens, haptens, enzymes, lectins, nucleic acids, repressors, oligo- and polynucleotides, protein A, protein G, avidin, streptavidin, biotin, complement component Clq, nucleic acid-binding proteins, etc. Specific binding pairs, include, but are not limited to, antibody-antigen, antibody-hapten, operator-repressor, nuclease-nucleotide, biotin-avidin, lectin-polysaccharide, steroid-steroid-binding protein, drug-drug receptor, hormone-hormone receptor, enzyme-substrate, IgG-protein A, complementary oligo- or polynucleotides, etc.

s. Tracer. Specific binding partners of the antibody employed for capture in an immunoassay (so-called capture antibody) include a so-called "tracer". A tracer as described herein incorporates a detectable label such as is known in the art that renders it capable of being detected and further is capable of binding (reacting with) the capture antibody. A tracer includes (a) a labeled analyte (e.g., a labeled hydrophobic drug such as an immunosuppressive); and (b) a labeled antigen or antigenic region of an analyte (e.g., a labeled antigen hydrophobic drug such as an immunosuppressive). A tracer also is referred to herein as a labeled specific binding partner, a "detection specific binding partner," and a "detection sbp."

t. Analyte binding protein. As used herein, "analyte binding protein" refers to endogenous protein present in a test sample that is capable of binding an analyte of interest. Since such analyte binding protein may interfere with an immunoassay, generally it is removed from binding to the analyte, e.g., by pretreatment of the sample with a pretreatment reagent.

u. Subject. As used herein, the terms "subject" and "patient" are used interchangeably irrespective of whether the subject has or is currently undergoing any form of treatment. As used herein, the terms "subject" and "subjects" refer to an animal, in one aspect, a bird (for example, a duck or goose), in another aspect, a shark or whale, or in a further aspect, a mammal including, a non-primate (for example, a cow, pig, camel, llama, horse, goat, rabbit, sheep, hamsters, guinea pig, cat, dog, rat, and mouse) and a primate (for example, a monkey, such as a cynomolgous monkey, chimpanzee, and a human).

v. Test sample. As used herein, the term "test sample" refers to a component, tissue or fluid from a subject's body which is the source of the immunosuppressant drug analyte. These components are well known in the art. For example, a test sample can be any biological sample derived from serum, plasma, whole blood, lymph, CNS fluid, urine, lymph fluids, or other bodily fluids of a subject. In one embodiment according to the disclosure, the test sample is whole blood. The test sample can be obtained using routine techniques known to those skilled in the art.

II. Diagnostic Immunoassays

Unless remedied by use of a specific antibody that does not cross-react with metabolites (i.e., binding competitors), or by the disclosure as described herein, one or more binding competitors present in a test sample can compete with one or more other molecules for binding to an epitope of interest or can interfere with the binding of one or more other molecules to an epitope of interest in the test sample. Specifically, one or more binding competitors can alter the assay characteristics of a test sample by displacing or preventing binding of an analyte of interest to another component of the test sample. In determining whether this is occurring, an assay diluent comprising one or more binding competitors can be used as described herein to determine the degree of cross-reactivity an antibody has for one or more binding competitors, and can be used to provide conditions for an immunoassay with improved (i.e., lowered) cross-reactivity to one or more binding competitors. Along these lines, the present disclosure provides among other things for the improvement of assay quantitation of active parent drug (e.g., immunosuppressant such as cyclosporine, tacrolimus, sirolimus or everolimus) in the presence of one or more of their respective major metabolites (e.g., M-I, M-II, and/or M-III for tacrolimus; e.g., M1, M8, M9, M13, M17, M18 and/or M21 for cyclosporine; e.g., 11-Hydroxy-sirolimus, 41-O-demethyl-sirolimus, 7-O-demethyl-sirolimus, and/or 41-O-demethyl-hydroxy-sirolimus for sirolimus).

Understanding of the disclosure will be facilitated by reference to the following sections "Exemplary Immunoassay," and "Immunoassays Generally."

A. Exemplary Immunoassay

Figure 4:
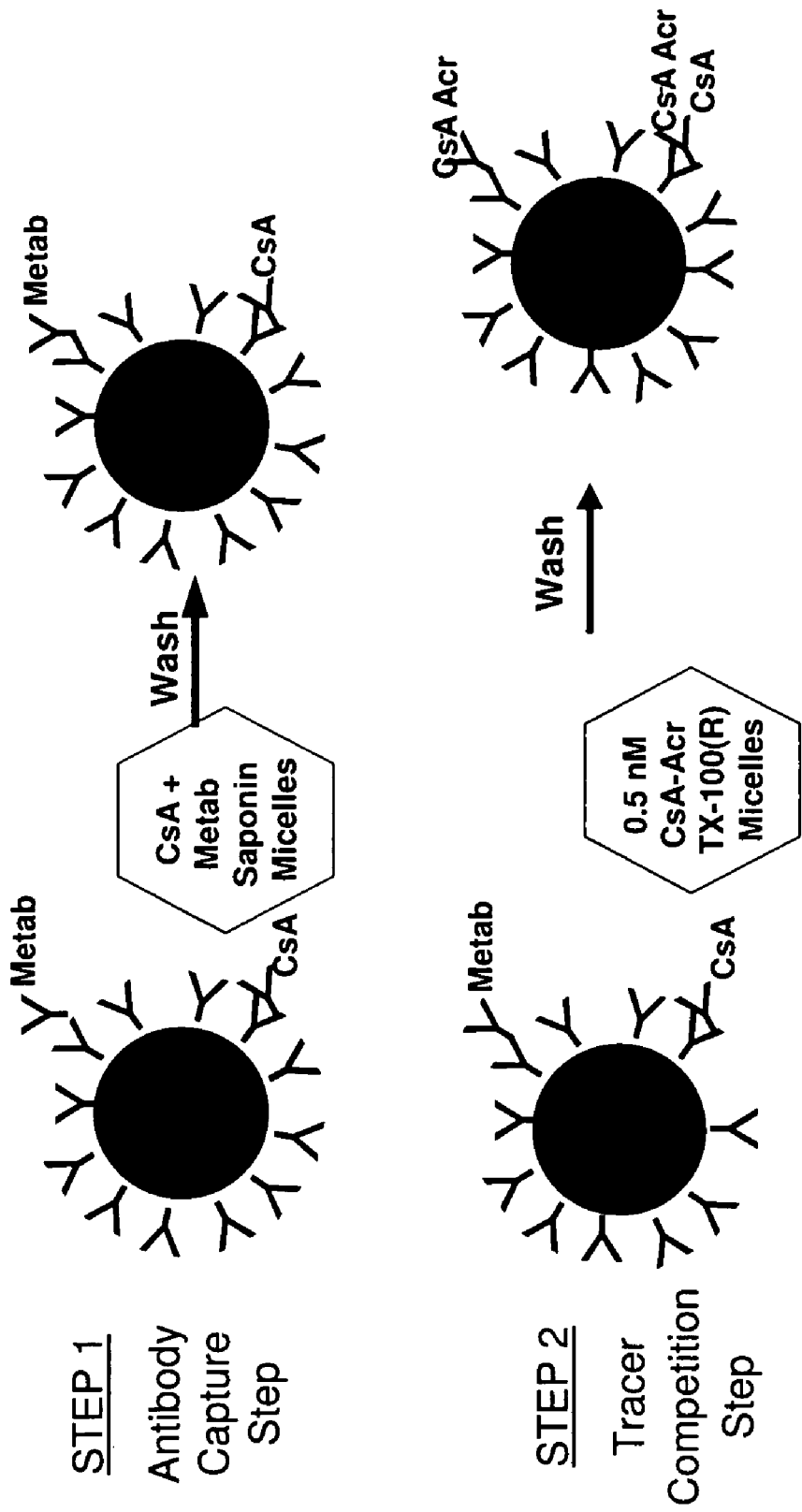
FIG. 4 shows an exemplary 2-step immunoassay according to the disclosure which is further described in section II (Diagnostic Immunoassays) "A. Exemplary Immunoassay."

An exemplary preferred two-step assay according to the disclosure is depicted in FIG. 4, and involves an antibody capture step (Step 1), and a tracer competition step (Step 2). The diagram in FIG. 4 pertains to the immunosuppressant CsA (one embodiment of the disclosure), but is applicable and readily adapted to other immunosuppressants (e.g., tacrolimus, sirolimus, everolimus, zotarolimus, temsorolimus MMF, MPA, and the like) and other hydrophobic drugs that metabolize in vivo or in vitro to form cross-reacting metabolites.

Organic solvents and detergents present in the sample pretreatment (e.g., methanol, ethylene glycol, saponin) all help solubilize hydrophobic drug (e.g., CsA) and cross-reacting metabolites (e.g., "CsA+Metab") in the extracted blood sample. The extracted sample is further diluted in the antibody capture step, where the solvent environment switches from organic solvent to a primarily aqueous mixture. Water insoluble drug and metabolites now become sequestered in the water soluble detergent phase. Under these conditions, detergents are known to form micellar structures, the size and structure of which are influenced by salt concentration, detergent type and temperature. Other hydrophobic reagent components such as antifoam (e.g., Poly Dimethyl Siloxanes) may also be present and can participate in drug sequestration. Antibody binding of drug and metabolites occurs in this aqueous, detergent-rich environment.

In the first step, monoclonal antibody present on the microparticles (depicted as Y-shaped structures on spheres) preferably is present in an amount of about 0.2 nM for assay of test sample which is anticipated to comprise from about 10 to about 100 nM of analyte immunosuppressive such as CsA, and up to four times the amount of the immunosuppressive of metabolite. Only about 1% of the immunosuppressant (CsA) and metabolite from the sample can be bound to antibody on the microparticles. Remaining unbound immunosuppressant and metabolite are removed in a wash step.

The tracer competition step (Step 2) optionally includes NaCl and antifoam present in the reaction that further comprises tracer (labeled immunosuppressant such as acridinylated CsA, "CsA-Acr"), and detergent (reduced Triton® X-100, "TX-100(R)"). Reduced Triton® X-100 is Triton® X-100 in which the benzene ring has been reduced to a cyclohexane ring. Optionally both Triton® X-100 and reduced Triton® X-100 can be used in the invention. In some embodiments, use of Triton® X-100 is preferred. In the second step, immunosuppressant, metabolite and tracer compete for available antibody sites, followed by a wash step and signal measurement. In this second step, the amount of immunosuppressant (e.g., CsA) present on the microparticles ranges from about 0.1 to about 1 nM, and about 0.5 nM tracer is employed. Without wishing to be bound by any theory, it appears that in the two-step format, reducing the immunosuppressant (e.g., CsA) and metabolite concentrations by approximately 100-fold in the tracer competition step allows drug binding selectivity, due to favorable differences in antibody dissociation constants for drug and metabolite. In particular, this means that immunosuppressant (such as CsA), metabolite and tracer are all competing at very low concentrations (less than 1 nM), close to the $K_D$ concentration for the immunosuppressant (such as CsA) where 50% binding occurs. One would expect the $K_D$ for metabolite binding to be much higher (i.e., a reflection of weaker binding). At metabolite concentrations well below the metabolite $K_D$ very little metabolite will bind to antibody, particularly in a competitive situation, where tight binding by CsA and tracer are present. This would result in no significant or very low cross-reactivity (or interference) by metabolites.

B. Immunoassays Generally

In other aspects, the present disclosure relates to diagnostic immunoassays that can be used for the qualitative and/or quantification of a hydrophobic drug as analyte (e.g., an immunosuppressive agent) in a test sample. The diagnostic immunoassays of the present disclosure can be conducted using any format known in the art, such as, but not limited to, a competitive inhibition format. A preferred format is a two-step competition assay involving antibody capture in a first step, and tracer competition in a second step, and including at least one wash step. Optimally the competition assay is preceded by sample pretreatment as described herein.

In other aspects, the present disclosure relates to diagnostic immunoassays that can be used for the qualitative and/or quantification of a hydrophobic drug as analyte (e.g., an immunosuppressive agent) in a test sample. In particular, the disclosure relates to immunoassays for hydrophobic drug that metabolizes to form one or more cross-reacting metabolites either in vivo (i.e., prior to isolation of the test sample) or in vitro (e.g., following isolation of the test sample, such as during sample handling and/or storage). The diagnostic immunoassays of the present disclosure can be conducted using any immobilized antibody format known in the art.

Optimally the competition assay is preceded by sample pretreatment as described herein (e.g., Examples, and Section IV). The sample pretreatment generally comprises contacting the test sample with one or more pretreatment reagents so as to form a first mixture. The pretreatment reagent lyses any cells and releases the analyte from any analyte binding proteins present in the test sample. Optionally any analyte binding proteins are removed from the first mixture (e.g., using one or more pretreatment reagents to precipitate proteins from the first mixture). In one embodiment the precipitated analyte binding proteins are removed (heterogeneous pretreatment) whereas in another embodiment the analyte binding proteins are soluble and are not removed (homogeneous pretreatment). Release of the analyte binding proteins from the drug analyte, however, is done to prevent any potential for interference in the immunoassay.

In such competitive immunoassays for the detection of analyte in a test sample suspected of containing or that is known to contain analyte (e.g., immunosuppressive agent), the test sample is contacted with at least one antibody that binds to at least one epitope of the analyte to form an antibody-analyte immune complex. The antibody employed (a so-called "capture antibody") optionally is immobilized on a solid phase. The antibody is specific for (i.e., is a specific binding partner of) the analyte. Such an antibody need not be optimized for reduced cross-reactivity to any cross-reacting metabolites that may be present in the sample. By virtue of the surprising and unexpected results described herein, it is possible to carry out the immunoassay in such a fashion that cross-reactivity with any one or more cross-reacting metabolites present in the sample is reduced to less than 10%, even in a situation where in other assays not performed as recommended herein the capture antibody cross-reacts with metabolite at a level greater than 10%.

The antibodies described in Section III herein can be used in such immunoassays to form such antibody-analyte (e.g., immunosuppressive agent) complexes in a second mixture derived from pretreated test sample (first mixture). Optionally the amount of antibody in the second mixture is from between about 0.1% and about 10% of the amount of analyte present in the test sample, especially between about 0.5% and about 2%, particularly about 1%.

Of course the antibody specific for the analyte also can form in the second mixture a complex with any one or more cross-reacting metabolites present in the test sample. Accordingly, washing of the second mixture is done to remove any analyte and metabolite not complexed with antibody. All wash steps described herein are done such as is known in the art using an appropriate wash buffer. As a consequence of such washing, a third mixture is formed in which the analyte concentration is decreased to near the equilibrium dissociation constant ($K_D$) of the antibody for analyte. By "near the $K_D$" is meant a value that is within about one order of magnitude of the $K_D$ of the antibody for analyte, i.e., a change of about one decimal point. Optionally "near the $K_D$" is within about half an order of magnitude of the $K_D$ of the antibody for analyte, i.e., a change of about half a decimal point.

Also, as a consequence of such washing, the analyte (e.g., CsA) and metabolite concentrations are decreased in the third mixture by from about 10-fold to about 1000-fold, especially by from about 10-fold to about 500-fold as compared to in the test sample. Optionally these concentrations are decreased by from about 50-fold to about 250-fold, or from about 75-fold to about 200-fold, or by about 100-fold. Of course, other ranges also are encompassed by the disclosure since the range depends on the ratio of the $K_D$s for hydrophobic drug and metabolite, as well as the initial hydrophobic drug/metabolite concentration present before the antibody capture step.

Subsequently, the third mixture is contacted with a specific binding partner of the antibody labeled with a detectable label (e.g., a so-called "detection sbp" or "tracer") to form a fourth mixture comprising an antibody-specific binding partner complex. In this fourth mixture, the specific binding partner binds only to those sites on the capture antibody which are not occupied/complexed with either analyte or metabolite. Following washing of the fourth mixture to remove specific binding partner not complexed with antibody, the antibody-specific binding partner complex is detected as a measure of the amount of analyte present in the sample. The amount of the antibody-specific binding partner complex is inversely proportional to the amount of analyte present in the sample. In such an immunoassay, there is less than about 10% cross-reactivity with any one or more cross-reacting metabolites present in the sample. Optionally there is less than about 7% cross-reactivity, less than about 5% cross-reactivity, less than about 4% cross-reactivity, less than about 3% cross-reactivity, less than about 2% cross-reactivity, less than about 1% cross-reactivity, less than about 0.5% cross-reactivity, less than about 0.3% cross-reactivity, less than about 0.2% cross-reactivity, or less than about 0.1% cross-reactivity. In most cases, the detection of the lowest amount of cross-reactivity is limited by the sensitivity (i.e., limit of detection) of the assay, which in the case of the CsA assay described herein appears to be about 0.1%. However, the lower limit may vary in another assay according to the disclosure, for instance, based on assay precision, the amount of signal, and other factors (e.g., access to later-developed and potentially more sensitive detection technology).

Moreover, because of the manner in which the immunoassay is carried out, preferably in the fourth mixture where tracer competition takes place, the volume is reduced as compared to in the second mixture where antibody capture takes place such that the concentration of the antibody present in the tracer competition step fourth mixture is decreased from within about 8-fold to about 3-fold, especially from within about 7-fold to about 4-fold, particularly within about 5-fold of the antibody present in the antibody capture step second mixture. In the fourth mixture where tracer competition takes place, the volume of the mixture ranges from about 20 µL to about 80 µL, especially from about 30 µL to about 70 µL, optionally from about 40 µL to about 60 µL, and particularly about 50 µL. In the second mixture where antibody capture takes place, the volume of the mixture ranges from 100 µL to about 400 µL, especially from about 150 µL to about 350 µL, optionally from about 200 µL to about 300 µL, and particularly about 250 µL, about 225 µL, about 200 µL, or about 175 µL.

In one embodiment, the amount of analyte present in a complex with antibody ranges from about 0.01 to about 10 nM (especially from about 0.1 to about 1.0 nM), and the specific binding partner (tracer) is present in an amount from between about 0.1 and about 1.0 nM (especially about 0.5 nM).

Detection of these immune complexes is done using routine techniques known to those skilled in the art. For example, the specific binding partner of the present disclosure can be labeled with a detectable label to detect the presence antibody-analyte complex (i.e., an inversely proportional relationship). Detectable labels and their attachment to specific binding partner such as an antigenic portion of a hydrophobic drug analyte (e.g., immunosuppressive agent) are discussed in more detail infra.

In a preferred embodiment, an aliquot of a labeled antigen of at least one immunosuppressive agent of a known concentration is used to compete with at least one immunosuppressive agent and any cross-reacting metabolite thereof in a test sample for binding to an antibody (such as a capture antibody of the present disclosure) in a competitive assay format. Antigens of immunosuppressive agents and methods of making the antigens are well known in the art and are commercially available. The immunosuppressive agent or antigen of the immunosuppressive agent can be labeled with any detectable label known to those skilled in the art. For example, but not limiting, the detectable label can be a radioactive label, such as, $^3H$, $^{125}I$, $^{35}S$, $^{14}C$, $^{32}P$, $^{33}P$, an enzymatic label, such as horseradish peroxidase, alkaline peroxidase, glucose 6-phosphate dehydrogenase, etc., a chemiluminescent label, such as, acridinium esters, luminal, isoluminol, thioesters, sulfonamides, phenanthridinium esters, etc., a fluorescence label, such as, fluorescein (5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry*, $2^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg. For example, as described in the Examples herein, acridinium-CsA antigen or other labeled immunosuppressive (e.g., biotinylated CsA or other immunosuppressive) can be used in the competitive format.

In one embodiment, the immunoassay relates an amount of the antibody-specific binding partner (i.e., tracer) complex formed to the amount of the analyte in the test sample either by use of a standard curve for the analyte, or by comparison to a reference standard. Any well known means for determining the amount of analyte (e.g., as set forth in the Examples) can be employed.

The immunosuppressive agent (or antigen of the immunosuppressive agent) can be labeled with any detectable label known to those skilled in the art to comprise the so-called tracer. In one embodiment, the capture antibody of the present disclosure can be immobilized on to a solid support. Moreover, if necessary or desired, the solid support can be derivatized to allow reactivity with various functional groups on the antibody. Such derivatization optionally involves the use of certain coupling agents such as, but not limited to, maleic anhydride, N-hydroxysuccinimide and 1-ethyl-3-(3-dimethylaminopropyl)carbodiimide. Alternatively, the capture antibody of the present disclosure can be coupled to another antibody, such as an antispecies antibody, that has been immobilized on to a solid support, such as a microparticle (See, e.g., Examples). Such an approach is an example of an antibody (a particular specific binding partner) that comprises multiple binding partners. The labeled specific binding partner (e.g., tracer), like the capture antibody, can comprise multiple binding partners. With use of a tracer that comprises multiple binding partners, it may be possible to make use of binding partners having different binding strengths or affinity to alter the characteristics of the assay.

The labeled specific binding partner (e.g., labeled immunosuppressive agent or antigen of immunosuppressive agent, or so-called tracer), the test sample analyte and the antibody are incubated in order to allow for the formation of antibody-analyte complexes. Generally speaking, the various incubations in the immunoassay (e.g., incubation of the first mixture for a first incubation period, incubation of the second mixture for a second incubation period, and incubation of the fourth mixture for a third incubation period) can be carried out at a pH of from about 4.0 to about 9.0, at a temperature of from about 2° C. to about 45° C. (especially from about 33° C. to about 38° C.), and for a period from at least about two (2) minutes to about eighteen (18) hours, preferably from about 2 minutes to about 24 minutes, most preferably from about 4 minutes to about 18 minutes.

Preferably the first incubation period (i.e., pretreatment step) comprises a period of from about 2 minutes to about 60 minutes. Preferably the second incubation period (i.e., antibody capture step) comprises a period of from about 2 minutes to about 30 minutes, especially from about 15 minutes to about 25 minutes, particularly about 22 minutes, about 20 minutes, about 18 minutes, or about 16 minutes. Preferably the third incubation period (i.e., tracer competition step) comprises a period of from about 2 minutes to about 30 minutes, especially from about 2 minutes to about 8 minutes, particularly about 6 minutes, about 5 minutes, about 4 minutes, or about 3 minutes.

Typically, at least two different species of antibody complexes are generated in the antibody capture step and tracer competition step. Specifically, in the antibody capture step one of the antibody complexes generated is with analyte and another is with any cross-reacting analyte metabolite. In the tracer competition step, both these sorts of complexes may be present in some amount, and additionally, a complex of tracer (specific binding partner having a detectable label) with the antibody also is formed. Preferably unbound tracer is separated from the remainder of the mixture and the amount of detectable label complexed with the antibody is then quantified by radioactive, fluorescent, chemiluminescent, enzymatic or other means known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label (e.g., acridinium, as described in the Examples), the label is quantified detecting the light emitted either visually or by using luminometers, x-ray film, high speed photographic film, a CCD camera, etc. The concentration of the analyte (e.g., immunosuppressive agent) in the test sample can then be determined by comparing the quantity of detectable label complexed with antibody to a standard curve. The standard curve can be generated using serial dilutions of the analyte (e.g., immunosuppressive agent) of known concentration, by mass spectroscopy, gravimetrically and by other techniques known in the art.

In the antibody capture step which preferably precedes tracer competition, the antibody-analyte (e.g., immunosuppressive agent) complex can be separated from the test sample mixture by binding the antibody to a solid support, and then removing the remainder of the test sample from contact with the solid support. For example, if the capture antibody is bound to a solid support such as a well or a bead, separation can be accomplished by removing the fluid (from the test sample mixture) from contact with the solid support. Optionally separation is accompanied by washing with a wash buffer. Optionally the solid support (e.g., so-called "solid phase") is any appropriate solid support or phase such as is known in the art. For instance, optionally the solid phase is selected from the group consisting of a magnetic particle, bead, test tube, microtiter plate, cuvette, membrane, a scaffolding molecule, film, filter paper, disc, and chip. Washing of solid phases between reactions can be accomplished using wash solutions and fluidic techniques known in the art. The preferred solid phase is a magnetic microparticle and a preferred wash buffer contains salt and non-ionic detergent.

Thus, in one embodiment, provided herein is an immunoassay for assessing the amount of cyclosporine in a test sample wherein one or more cross-reacting metabolites of cyclosporine also may be present, the immunoassay comprising the steps of:

(a) contacting the test sample with one or more pretreatment reagents to form a first mixture, wherein the one or more pretreatment reagents lyse any cells and solubilize any analyte present in the test sample;

(b) contacting the first mixture with an antibody specific for cyclosporine and that is immobilized on a solid phase to form a second mixture comprising a complex of the antibody with cyclosporine or a metabolite of cyclosporine;

(c) washing the second mixture to remove any analyte and any cyclosporine metabolite not complexed with the antibody and to form a third mixture in which the cyclosporine concentration is decreased to near the equilibrium dissociation constant (KD) of the antibody for cyclosporine;

(d) contacting the third mixture with cyclosporine labeled with a detectable label such as acridinium ("tracer") to form a fourth mixture comprising an complex of the antibody with tracer ("antibody-tracer complex");

(e) washing the fourth mixture to remove any tracer not complexed with antibody; and (f) detecting the antibody-tracer complex as measure of the amount of cyclosporine present in the sample, wherein the immunoassay has less than about 10% cross-reactivity (or alternately less than about 5% cross-reactivity) with any one or more cross-reacting metabolites of cyclosporine present in the sample.

In one aspect of this immunoassay, optionally the amount of antibody in step (b) is from between about 0.1% and about 10% of the amount of cyclosporine present in the test sample. Further, optionally the cyclosporine and metabolite concentrations are decreased in the third mixture in step (c) by from about 10-fold to about 500-fold as compared to in the test sample. Additionally, optionally in step (d) the amount of cyclosporin present in a complex with antibody ranges from about 1.0 and about 10.0 nM, and the tracer is present in an amount from between about 0.1 to about 1.0 nM. Moreover, optionally the antibody in step (b) has a KD for cross-reacting cyclosporin metabolite that is between about 10-fold and about 1000-fold higher than for analyte.

In another aspect of the immunoassay, the test sample is whole blood. Optionally, the cyclosporin metabolite is selected from the group consisting of M1, M8, M9, M13, M17, M18, M21 and combinations thereof. In particular, the cyclosporin metabolite can be M1 or M9.

The immunoassays described herein (i.e., the cyclosporine immunoassay or the other immunosuppressive drug immunoassays) optionally can be carried out to monitor patients receiving immunosuppressive therapy (e.g., for treatment of organ or tissue rejection following transplant surgery, of graft versus host disease or of autoimmune disease), and further optionally can be employed to assist the physician with making therapeutic decisions. Along these lines, the present disclosure also provides a method of monitoring the course of treatment of a subject with an immunosuppressive drug (e.g., cyclosporine) that metabolizes to form one or more cross-reacting metabolites, the method comprising the steps of:

(a) providing a test sample;

(b) determining the concentration of immunosuppressive drug (e.g., cyclosporine) in the test sample according to the immunoassays described herein; and (c) comparing the concentration of immunosuppressive drug (e.g., cyclosporine) in the test sample determined in step (b) with a predetermined level (well known for immunosuppressive drugs).

In another aspect, this method comprises the steps of:

(a) providing a first test sample from the subject before the subject has been administered an immunosuppressive drug (e.g., cyclosporine);

(b) determining the concentration of immunosuppressive drug (e.g., cyclosporine) in the first test sample;

(c) comparing the concentration of immunosuppressive drug (e.g., cyclosporine) determined in step (b) with a predetermined level;

(d) treating the subject with an immunosuppressive drug (e.g., cyclosporine) for a period of time if the comparison of the concentration of immunosuppressive drug (e.g., cyclosporine) determined in step (c) with the predetermined level so warrants;

(e) providing a second and/or subsequent test samples from the subject after the subject has been administered immunosuppressive drug (e.g., cyclosporine);

(f) determining the concentration of immunosuppressive drug (e.g., cyclosporine) in the second and/or subsequent test samples;

(g) comparing the concentrations of immunosuppressive drug (e.g., cyclosporine) determined in step (f) with the concentration of immunosuppressive drug (e.g., cyclosporine) determined in step (b).

According to these methods, treatment can be altered if the measured concentration of immunosuppressive drug (e.g., cyclosporine) is higher or lower than a recommended predetermined level, or if a trend in levels (increase or decrease) based on a prior measured level suggests that treatment should be altered.

III. Antibodies

The antibodies for use in the immunoassays of the present disclosure can be prepared using routine techniques known to those skilled in the art, or are commercially available.

For example, optionally a CsA assay can be done using for a capture antibody the antibodies described herein, using any of the antibodies described in the extensive literature on CsA assays, using any of the commercially available antibodies specific for CsA, or using antibody-containing components of any of the commercially marketed kits for conducting CsA assays. Likewise, a tacrolimus, sirolimus or other immunosuppressive assay according to the disclosure can be done using as a capture antibody any of the antibodies described in the extensive literature on tacrolimus, sirolimus and other immunosuppressive assays, using any of the commercially available antibodies specific for tacrolimus, sirolimus or other immunosuppressives, or using antibody-containing components of any of the commercially marketed kits for conducting tacrolimus, sirolimus or other immunosuppressive assays.

In particular, other Anti-Cyclosporine monoclonal antibodies that can be employed include monoclonal mouse anti-cyclosporin A [catalog number RDI-TRK3C13-CSZ.22, RDI Division of Fitzgerald Industries Intl, Concord, Mass.]. Other Anti-Tacrolimus monoclonal antibodies that can be employed include FKBP1B monoclonal antibody (M01), clone 4H5-1B6 [catalog number H00002281-M01, Abnova Corporation, Taipei City, Taiwan] and monoclonal mouse anti-FK506 [catalog number 4FK42, HyTest Ltd., Turku Finland]. Other Anti-Sirolimus monoclonal antibodies that can be employed include monoclonal mTOR antibody [catalog number 2972 Cell Signaling Technology, Beverly, Mass.].

Antibodies useful in the immunoassay methods of the disclosure include both polyclonal and monoclonal antibodies. Polyclonal antibodies are raised by injecting (e.g., subcutaneous or intramuscular injection) an immunogen into a suitable non-human mammal (e.g., a mouse, goat or rabbit). Generally, the immunogen should induce production of high titers of antibody with relatively high affinity for the target antigen.

If desired, the endogenous antigen (i.e., analyte of interest) may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal.

The antibodies are then obtained from blood samples taken from the animal. The techniques used to produce polyclonal antibodies are extensively described in the literature (see, e.g., Methods of Enzymology, "Production of Antisera With Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies see, for example, Coligan, et al. (1991) Unit 9, Current Protocols in Immunology, Wiley Interscience.

For many applications, monoclonal antibodies (mAbs) are preferred because their binding specificity is constant and can be well characterized. The general method used for production of hybridomas secreting mAbs is well known (See, Kohler, et al., *Nature*, 256:495 (1975)). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody that bound to cancer cell lines. Confirmation of specificity among mAbs can be accomplished using routine screening techniques (such as the enzyme-linked immunosorbent assay, or "ELISA") to determine the elementary reaction pattern of the mAb of interest.

As used herein, the term "antibody" encompasses antigen-binding antibody fragments, e.g., single chain antibodies (scFv or others), which can be produced/selected using known phage display or yeast display technology (i.e., by in vitro affinity maturation of the antibody). The ability to express antibody fragments on the surface of viruses that infect bacteria (bacteriophage or phage) makes it possible to isolate a single binding antibody fragment, e.g., from a library of greater than 1010 nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) *Nature*, 348: 552-554 (1990); Hoogenboom et al., *Nucleic Acids Res.* 19: 4133-4137 (1991)). Yeast display affinity maturation is discussed, e.g., in PCT WO 2007/056507, hereby incorporated by reference in its entirety for its teachings regarding the same.

In one aspect, the antibodies of the present disclosure can be prepared by recombinant expression of immunoglobulin light and heavy chain genes in host cells. To express an antibody recombinantly, a host cell is transfected with one or more recombinant expression vectors carrying nucleic acid molecules encoding the immunoglobulin light and heavy chains of the antibody such that the light and heavy chains are expressed in the host cell and, preferably, secreted into the medium in which the host cells are cultures, from which medium the antibodies can be recovered. Standard recombinant nucleic acid (DNA) methodologies are used to obtain antibody heavy and light chain genes, incorporate these genes into recombinant expressions vectors and introduce the vectors into host cells, such as those described in Sambrook, Fritsch and Maniatis (eds), *Molecular Cloning: A Laboratory Manual, Second Edition*, Cold Spring Harbor, N.Y., (1989), Ausubel, F. M. et al. (eds.) *Current Protocols in Molecular Biology*, Greene Publishing Associates (1989) and in U.S. Pat. No. 4,816,397.

Preferred mammalian host cells for expressing the recombinant antibodies of the disclosure include the CHO cells (including dhfr-CHO cells, described in Urlaub and Chasin, *Proc. Natl. Acad. Sci. USA* 77:4216-4220 (1980), used with a DHFR selectable marker, for example, as described in R. J. Kaufman and P. A. Sharp, *Mol. Biol.* 159:601-621 (1982)), NSO myeloma cells, COS cells, HEK-293 cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments, F(ab') fragments or scFv molecules. It will be understood that variations on the above procedure are within the scope of the present disclosure. For example, it may be desirable to transfect a host cell with nucleic acid molecule encoding either the light chain or the heavy chain (but not both) of an antibody of the present disclosure. Recombinant DNA technology may also be used to remove some or all of the nucleic acid molecules encoding either or both of the light and heavy chains that are not necessary for binding to at least one epitope on at least one immunosuppressive agent. The molecules expressed from such truncated nucleic acid molecules also are encompassed by the antibodies of the disclosure.

IV. Methods for Sample Pretreatment & Assay Component Compositions

The sample used in the method is the source of an analyte containing at least one epitope of interest. The sample can be a test sample from a subject or may not be derived from a subject but nonetheless comprises the analyte containing the epitope of interest (e.g., spiked sample, or sample from biological source other than a subject, such as water). The sample may further comprise (in addition to the analyte of interest) other components including but not be limited to, antibodies, antigens, haptens, hormones, drugs, enzymes, receptors, proteins, peptides, polypeptides, oligonucleotides or polynucleotides of interest. For example, the sample may be an immunosuppressive agent, such as tacrolimus or cyclosporine (e.g., a source of the drug itself, such as a commercial source). Alternatively, the sample may be a whole blood sample obtained from a subject that contains tacrolimus or cyclosporine. A preferred sample according to the disclosure is a test sample, particularly whole blood, especially whole blood that has been treated as described herein, e.g., with a pretreatment reagent.

One or more pretreatment reagents can be employed for certain of the hydrophobic drug analytes (e.g., immunosuppressants), but may not be needed for others. The pretreatment reagent can be a heterogeneous agent or a homogeneous agent.

With use of one or more heterogeneous pretreatment reagents according to the disclosure, the pretreatment reagent(s) precipitate(s) any analyte binding protein present in the sample. Such an assay comprises removing any analyte binding protein from the first mixture by separating the supernatant of the first mixture from the precipitated analyte binding protein. In such an assay, the supernatant of the first mixture absent any binding protein is used in the next step of the assay, the antibody capture step.

With use of one or more homogeneous pretreatment reagents there is no such separation step. The entire first mixture of test sample and one or more pretreatment reagents are contacted with the capture antibody in the antibody capture step. The one or more pretreatment reagents in such an assay typically are diluted in the pretreated test sample mixture, either before the antibody capture step or during encounter with the antibody in the antibody capture step. Despite such dilution, a certain amount of the one or more pretreatment reagents (for example, 5 M methanol and/or 0.6 M ethylene glycol) are still present (or remains) in the test sample mixture during antibody capture.

The one or more pretreatment reagents comprise: (a) one or more solvents and salt, (b) one or more solvents, salt and detergent, (c) detergent, or (d) detergent and salt. Solvents include methanol and ethylene glycol. Salts include zinc sulfate and sodium chloride. A preferred detergent for a pretreatment reagent is saponin. A preferred pretreatment reagent comprises about 70% methanol, about 20% ethylene glycol, and about 50 mM zinc sulfate.

The composition of pretreatment reagents optionally contain one or more organic solvents and detergents, as well as other components as needed for a specific assay method. Accordingly, in one embodiment of the immunoassay, the one or more pretreatment reagents comprise saponin, methanol, ethylene glycol and zinc sulfate, as described in the Examples and literature. Assay pretreatment reagents containing one or more organic solvents, such as a combination of methanol and ethylene glycol (and optionally zinc sulfate) also can be employed. Pretreatment reagents comprising saponin, either with or without added salt can be used. Moreover, pretreatment reagents for use in assays on TDx, AxSYM®, and ARCHITECT® analyzers can be employed (especially when optimized for a given assay), e.g., as described in the literature (see, e.g., Yatscoff et al., Abbott TDx Monoclonal Antibody Assay Evaluated for Measuring Cyclosporine in Whole Blood, *Clin Chem*, 36:1969-1973 (1990) and Wallemacq et al., Evaluation of the New AxSYM®Cyclosporine Assay: Comparison with TDx Monoclonal Whole Blood and EMIT Cyclosporine Assays, *Clin Chem* 45: 432-435 (1999)), and/or as commercially available (Abbott Laboratories, Abbott Park, Ill.).

Preferred methods of sample pretreatment are described herein (e.g., in the Examples). Additionally, pretreatment can be done as described in Abbott's U.S. Pat. No. 5,135,875, EP 0 471 293, U.S. Patent Application 60/878,017 filed Dec. 29, 2006; and U.S. patent application Ser. No. 11/490,624 filed Jun. 21, 2006 (incorporated by reference in its entirety for its teachings regarding pretreatment).

In another embodiment the second mixture comprises an assay diluent. Preferably the assay diluent is one that can be used without deleteriously impacting the reaction conditions of a diagnostic immunoassay. Preferably the assay diluent does not substantially alter the $K_D$ of the capture antibody. Optionally the assay diluent comprises at least one buffer, optionally salt, optionally detergent, and/or combinations thereof. Also, the assay diluent can be that of a commercially marketed assay, e.g., an assay for ARCHITECT®, or an assay (e.g., a CsA assay) for TDx or AxSYM® (Abbott Laboratories, Abbott Park, Ill.) especially when optimized for a given assay.

In another embodiment, the fourth mixture employed in the immunoassays herein further comprises a detergent. Optimally the detergent is Triton® X-100.

The immunoassays and methods described herein also can be adapted for use in a variety of automated and semi-automated systems (including those wherein the solid phase comprises a microparticle), as described, e.g., in U.S. Pat. Nos. 5,089,424 and 5,006,309, and as, e.g., commercially marketed by Abbott Laboratories (Abbott Park, Ill.) including but not limited to Abbott's ARCHITECT®, AxSYM®, IMx®, PRISM®, and Quantum™ II instruments, as well as other platforms. Moreover, the disclosure optionally is adaptable for the Abbott Laboratories commercial Point of Care (I-STAT®) electrochemical immunoassay system for performing sandwich immunoassays. Immunosensors, and their methods of manufacture and operation in single-use test devices are described, for example in, U.S. Pat. No. 5,063,081, U.S. Patent Application 2003/0170881, U.S. Patent Application 2004/0018577, U.S. Patent Application 2005/0054078, and U.S. Patent Application 2006/0160164, which are incorporated in their entireties by reference for their teachings regarding same.

V. Kits

The present disclosure also contemplates kits for detecting the presence of an analyte of interest (e.g., hydrophobic drug that metabolizes to form one or more cross-reacting metabolites) in a test sample. Such kits can comprise one or more of the antibodies described herein. More specifically, the kit optionally can contain (1) at least one antibody that has a $K_D$ for cross-reacting metabolite that is between about 10-fold and about 1000-fold higher than for analyte; and (2) one or more instructions for performing the immunoassay. The antibodies of the present disclosure can be included in such a test kit as a capture antibody, as a detection antibody or both as a capture antibody and a detection antibody. Alternatively, a tracer can be employed for detection. Any appropriate calibrator or control can be included in the kit (e.g., cyclosporine calibrator for a cyclosporine assay). Optionally, the kit can also contain at least one sample collection tube. Optionally, the kit can also contain at least one pretreatment reagent.

Thus, the present disclosure further provides for diagnostic and quality control kits comprising an immunoassay according to the present disclosure. Optionally the assays, kits and kit components of the invention are optimized for use on commercial platforms (e.g., immunoassays on the PRISM®, AxSYM®, ARCHITECT® and EIA (Bead) platforms of Abbott Laboratories, Abbott Park, Ill., as well as other commercial and/or in vitro diagnostic assays). Additionally, the assays, kits and kit components can be employed in other formats, for example, on electrochemical or other hand-held or point-of-care assay systems. The present disclosure is, for example, applicable to the commercial Abbott Point of Care (I-STAT®, Abbott Laboratories, Abbott Park, Ill.) electrochemical immunoassay system that performs sandwich immunoassays for several cardiac markers, including TnI, CKMB and BNP. Immunosensors and methods of operating them in single-use test devices are described, for example, in U.S. Patent Applications 2003/0170881, 2004/0018577, 2005/0054078 and 2006/0160164 which are incorporated herein by reference. Additional background on the manufacture of electrochemical and other types of immunosensors is found in U.S. Pat. No. 5,063,081 which is also incorporated by reference for its teachings regarding same.

Optionally the kits include quality control reagents (for example, sensitivity panels, calibrators, and positive controls). Preparation of quality control reagents is well known in the art, and is described, e.g., on a variety of immunodiagnostic product insert sheets.

The kits can optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), may also be included in the kit. The kit may additionally include one or more other controls. One or more of the components of the kit may be lyophilized and the kit may further comprise reagents suitable for the reconstitution of the lyophilized components. Alternately, kit components can be provided in ready to use form.

The various components of the kit optionally are provided in suitable containers. As indicated above, one or more of the containers may be a microtiter plate. Preferably, however, the kits are provided for use on a commercial automated assay. The kit further can include containers for holding or storing a sample (e.g., a container or cartridge for a blood or urine sample). Where appropriate, the kit may also optionally contain reaction vessels, mixing vessels and other components that facilitate the preparation of reagents or the test sample. The kit may also include one or more instruments for assisting with obtaining a test sample, such as a syringe, pipette, forceps, measured spoon, or the like.

The kit further can optionally include instructions for use, which may be provided in paper form or in computer-readable form, such as a disc, CD, DVD or the like.

Now by way of example, and not of limitation, examples of the present disclosure shall now be given.

Example 1

Investigation of Various Assay Formats

This example compares metabolite cross-reactivity in an immunoassay that combines a CsA blood extract with Tracer (acridinylated CsA), Antibody (anti-CsA antibody) bound to magnetic microparticles, and Assay Diluent (buffer and sodium chloride) in various formats, including a one-step or two-step format, and either with or without wash step(s).

For all four assay Formats described in this example (i.e., Formats 1-4), extraction of CsA from blood samples was accomplished by mixing 200 µL of blood sample (with or without added metabolite) with 100 µL of an aqueous saponin reagent, followed by 400 µL of methanol/ethylene glycol/zinc sulfate reagent in a 1.5 mL plastic centrifuge tube. The mixture was vortexed vigorously for 5-10 seconds and the resulting suspension was centrifuged at 13,000 rpm for 5 minutes to pellet a precipitate. The supernatant was assayed for CsA on an automated ARCHITECT® i2000 analyzer (Abbott Laboratories, Abbott Park, Ill.).

Other materials and methods employed herein and in subsequent examples were as follows:

Antibody. The anti-CsA monoclonal antibody used in the ARCHITECT® assay is immobilized on Goat Anti-Mouse (GAM) antibody coated magnetic microparticles. The same anti-CsA antibody is used in soluble form in the Abbott TDx and AxSYM® assays (Abbott Laboratories, Abbott Park, Ill.). Soluble mouse anti-CsA antibody is added directly to GAM microparticles and non-covalent binding occurs by antibody-mediated binding. GAM antibody is passively bound to magnetic polystyrene microparticles and then treated with a water-soluble carbodiimide to fix the antibody on the particle. GAM particles can be prepared using ordinary skill in the art.

Tracer. The CsA-Acridinium Tracer used in the assay is based on the acridinium chemistry used in the ARCHITECT® family of immunoassays. The Acridinium label is covalently attached to the same position on the CsA molecule as is the Fluorescein label in the TDx and AxSYM® tracer (e.g., as described in European Patent Application 0 283 801 A2 but differing in that an acridinium label, not fluorescein, is employed; see also, Mattingly et al., Chemiluminesent N-sulfonylacridinium-9-Carboxamides and their Application in Clinical Assays, *Luminescence Biotechnology Instruments and Applications* (Dyke K. V. Ed., CRC Press, Boca Raton) 2002; pp. 77-105).

Assay Diluent. Assay diluent for the following studies is that used in the ARCHITECT® family of immunoassays (i.e., containing MES buffer, NaCl and a preservative).

CsA Calibrators and Controls. The CsA used in calibrators is USP-grade purchased from United States Pharmacopeia (USP, Rockville, Md.). Calibrators are prepared in a processed, human whole blood matrix from ABT (American Biological Technologies, Inc., Seguin, Tex. 78155). CsA is dissolved in organic solvent and added to the blood matrix gravimetrically. The Calibrator concentrations are 0 ng/mL CsA (Calibrator A, or "CAL A"), 40 ng/mL CsA (Calibrator B, or "CAL B"), 150 ng/mL CsA (Calibrator C, or "CAL C"), 400 ng/mL CsA (Calibrator D, or "CAL D"), 800 ng/mL CsA (Calibrator E, or "CAL E") and 1500 ng/mL CsA (Calibrator F, or "CAL F"). Concentrations are checked against primary standards that use highly-purified CsA. Lyophilized human blood matrix Controls were purchased from BioRad Laboratories, Clinical Diagnostics, 4000 Alfred Nobel Drive, Hercules, Calif. 94547.

Specimens and Proficiency Samples. Blood specimens from transplant patients were acquired from Toronto General Hospital. Specimens were coded numerically and provided unlinked to patient information, following the ethics procedures of the hospital. Blood specimens were stored refrigerated for up to 1 month before use. Frozen samples were stored indefinitely at −20 C.

Previously-tested Proficiency samples used by clinical laboratories for Transplant drugs were obtained from Professor David W Holt, Analytical Services International Ltd., 5 Lavender Close, Chaldon Common, CATERHAM, CR3 5DW, UK. These samples were aliquots of pools of frozen patient specimens and spiked, drug free blood, which are supplied frozen quarterly at testing laboratories. CsA concentrations measured by different assay methods are the interlaboratory mean results reported to the proficiency survey and published on the internet at http://www.bioanalytics.co.uk/html.

Immunosuppressive Concentration. CsA concentration is calculated making use of the ARCHITECT®'s optics system, essentially a photomultiplier tube (PMT) that performs photon counting on the light emitted by the chemiluminescent reaction. The amount of light generated by the chemiluminescent reaction is directly proportional to the amount of acridinium tracer present in the reaction mixture, and is indirectly proportional to the amount of CsA. Signal is measured in RLUs (Relative Light Units), the designation for the unit of optical measurement on the ARCHITECT® system.

The term Relative Light Units comes from the relation of the photon counting to a certain amount of acridinium. Each optics module is calibrated with a set of acridinium standards. When the chemiluminescent reaction occurs, light is emitted and the photons are measured over a 3 second time period. The PMT converts the photons counted to digital signal, which is then sent to a circuit board for processing. The optics circuit board converts the digital signal from the PMT to an analog signal that is proportional to the photons counted, which is in turn proportional to the amount of acridinium present. This analog signal is then further processed to produce an RLU value. This relationship was established to produce a standard for calibration of the optics module, where the different acridinium standards have RLU values assigned to them. So, while the RLU unit itself is arbitrary, it is proportional (i.e., relative) to a certain amount of acridinium.

% CV. The % Coefficient of Variation is (CV) is defined as the standard deviation of a measurement (SD) divided by the mean analyte concentration and multiplied by 100.

B/A and F/A ratios. B/A and F/A are the ratios of RLU signals provided by the ARCHITECT® analyzer for Calibrators A, B and F.

% Cross-reactivity. Cross-reactivity results were determined based on the measured CsA concentration in the presence and absence of spiked cross-reacting metabolites. % Cross-reactivity was calculated as follows:

$$(\text{ng/mL } CsA \text{ in Spiked Sample} - \text{ng/mL } CsA \text{ in Control})/(\text{ng/mL Metabolite}) \times 100.$$

Metabolite Spiking Studies. Blood samples were spiked with 200 ng/mL CsA and either 0 ("Control") or 1000 ng/mL of Metabolite AM1 or AM9 (purified at Abbott Laboratories, Abbott Park, Ill. from in vivo-generated metabolite mixtures).

$K_D$ measurements. Binding constants of CsA for human albumin, bovine gamma globulin and anti-CsA antibody were determined by measuring fluorescence polarization of Fluorescein-labeled CsA tracer in solutions containing different concentrations of protein. Measurements were made and $K_D$s were calculated by methods described in Tetin, S. Y. and Hazlett, T. L., Optical Spectroscopy in Studies of Antibody-Hapten Interactions. *Methods* 20: 341-361 (2000). Purified human Albumin and Gamma Globulin were purchased from Celliance Corporation, Norcross, Ga. 30092 U.S.A. Anti-CsA antibody was purified at Abbott Laboratories by Protein A affinity chromatography, as described in Porous 50A Perfusion Chromatography Bulk Media for Protein A Affinity Chromatography, Operating Instructions. PerSeptive Biosystems. Rev. 2, 1994. pp. 1-7.

FPIA test methods. Abbott TDx Monoclonal and AxSYM® immunoassays were measured on specimens and calibrators using procedures described in the package inserts. Specimens were extracted with a combination of saponin, organic solvent and Zinc sulfate and precipitated protein was centrifuged down. The clear supernatant was tested using assay reagents (Tracer, Antibody and Assay Diluent). However, in Example 4, the different extraction (pretreatment) methods of TDx and AxSYM® were employed, but all results were generated on ARCHITECT®.

Other ARCHITECT® reagents. ARCHITECT® wash buffer, Pre-trigger and Trigger solutions used for the experiments described are standard for assays done on this instrument.

The four Assay Formats tested (Format 1, Format 2, Format 3, and Format 4) are discussed below.

Format 1—Immediate Tracer Addition in a 1-Step Assay Format

This format combines a CsA blood extract with Tracer and Antibody reagents in a first step, followed by diluent addition and a wash step. The assay Format 1 was done on an automated ARCHITECT® i2000 analyzer by:

1. Mixing 15 µL of sample extract with 90 µL of a Tracer and 50 µL of microparticles coated with goat anti-mouse antibody (from Sigma, St. Louis, Mo.) and mouse anti-CsA antibody (using antibody purified for use in fluorescence polarization immunoassays on TDx and AxSYM® instruments (Abbott Laboratories, Abbott Park, Ill.)).

2. Incubating the reaction mixture for 18 minutes at 33-38 degrees C. to allow competition to occur between CsA, a CsA metabolite and Acridinium-CsA Tracer for CsA binding sites on the antibody.

3. Mixing 50 μL of an Assay Diluent with the microparticle/tracer/sample reaction mixture and incubating for an additional 4 minutes at 33-38 degrees C.

4. Separating the microparticles magnetically from the reaction mixture and washing them with ARCHITECT® wash buffer to remove tracer and other liquid reactants.

5. Adding Pre-trigger (acid solution) and Trigger (basic solution) to cause the captured acridinium-CsA label to emit light, which is measured by the instrument as RLUs.

6. Comparing the RLU signal from unknown sample to RLUs generated during an assay calibration run using CsA standards.

7. Calculating a CsA concentration for the unknown sample using ARCHITECT® mathematical procedures.

Format 2—Immediate Tracer addition in a 2-step assay format

This format combines a CsA blood extract with Tracer and Antibody reagents in a first step, followed by a wash step. This is followed an Assay Diluent incubation step and a second wash step. The assay Format 2 was done on an automated ARCHITECT® i2000 analyzer by:

1. Mixing 75 μL of sample extract with 90 μL of a Tracer and 50 μL of the microparticles described above for Format 1.

2. Incubating the reaction mixture for 18 minutes at 33-38 degrees C. to allow competition to occur between CsA, a CsA metabolite and Acridinium-CsA Tracer for CsA binding sites on the antibody.

3. Separating the microparticles magnetically from the reaction mixture and washing them with ARCHITECT® wash buffer to remove tracer and reactants.

4. Resuspending the washed particles in 50 μL of an Assay Diluent and incubating for an additional 4 minutes at 33-38 degrees C.

5. Separating the microparticles magnetically from the reaction mixture and washing them again with ARCHITECT® wash buffer to remove liquid reactants.

6. Comparing the RLU signal measured from sample and standards and determining CsA concentration as described for Format 1.

Format 3—Delayed Tracer Addition in a One-Step Assay Format

This format is as for Format 1 except that Tracer and Assay Diluent are switched. Thus 90 μL of Assay Diluent is added in the initial incubation (step 1) and 50 μL of Tracer is added in the second incubation (step 3). This assay employs a single wash step as in Format 1. The assay Format 3 was done on an automated ARCHITECT® i2000 analyzer.

Format 4—Delayed Tracer Addition in a 2-Step Assay Format

This format is as for Format 2, except that Tracer and Assay Diluent are switched. Thus 90 μL of Assay Diluent is added in the initial incubation (step 1) and 50 μL of Tracer is added in the second incubation (step 3). This assay employs two separate wash steps. The assay Format 4 was done on an automated ARCHITECT® i2000 analyzer.

The various assay formats are summarized in Table 1 in terms of the concentrations of Tracer, metabolite and Antibody binding sites. The binding site concentration is twice the antibody concentration because there are two antibody binding sites. Since the extracted samples contain saponin detergent (Desert King, Lexington, Ky.) and the Tracer contains chemically-reduced Triton® X-100 ("TX100," from Sigma, St Louis, Mo.). The presence or absence of these detergents is also noted in Table 1. Detergents are responsible for solubilizing hydrophobic compounds such as CsA, metabolite and Tracer. They may also play an important role in controlling the amounts of these components that are free in solution versus sequestered in detergents. Saponin is present at 80-300 μM concentrations and TX100 is in the range of 140-1900 μM. These concentrations are both well above the critical micelle concentrations for the detergents, so it is expected that saponin and TX100 are present in micelle form.

TABLE 1

| | | Format 1 One Step | | Format 2 Two Step | |
|---|---|---|---|---|---|
| | Assay Type | $1^{st}$ incubation | $2^{nd}$ incubation | $1^{st}$ incubation | $2^{nd}$ incubation |
| Tracer Addition First Incubation Step | Antibody, nM | 0.32 | 0.24 | 0.23 | 1.0 |
| | Metabolite, nM | 23 | 17 | 83 | <1.0 |
| | Tracer, nM | 0.29 | 0.22 | 0.21 | <0.2 |
| | Saponin | Present | Present | Present | Absent |
| | Triton ® X-100 | Present | Present | Present | Absent |
| | | Format 3 One Step | | Format 4 Two Step | |
| | Assay Type | $1^{st}$ incubation | $2^{nd}$ incubation | $1^{st}$ incubation | $2^{nd}$ incubation |
| Tracer Addition Delayed until 2nd Incubation | Antibody, nM | 0.32 | 0.24 | 0.23 | 1.0 |
| | Metabolite, nM | 23 | 17 | 83 | <1.0 |
| | Tracer, nM | None | 0.12 | None | 0.50 |
| | Saponin | Present | Present | Present | Absent |
| | Triton ® X-100 | Absent | Present | Absent | Present |

The cross-reactivity values observed with the various assay formats are summarized in Table 2. These results confirm the reduced cross-reactivity observed with use of assay Format 4.

TABLE 2

| | Format 1 One Step | | Format 2 Two Step | |
|---|---|---|---|---|
| Cross-reactivity | AM 1 | 8% | AM 1 | 8% |
| | AM9 | 22% | AM9 | 17% |
| | Format 3 One Step | | Format 4 Two Step | |
| Cross-reactivity | AM 1 | 45% | AM 1 | <1% |
| | AM9 | 88% | AM9 | <1% |

Example 2

The Effect of Detergents in the ARCHITECT® Tracer Reagent

This example shows that the detergent chosen to block Tracer affects both the curve shape and assay precision.

The assay was performed as in Example 1, Format 4 (Delayed Tracer addition in the 2-Step Assay format), using Tracer containing different detergents at a concentration of 0.05%. Detergents were purchased from Sigma Chemical Co (St. Louis, Mo.).

Results of these experiments are depicted in Table 3, which summarizes RLU signal, curve shape (B/A and F/A RLU ratios), and mean Calibrator concentration precision (coefficient of variation, "CV"), expressed as a % CV. Low B/A ratios correlate with the best assay sensitivity. High F/A ratios are correlated with high Tracer non-specific binding (NSB) to the surface of the plastic reaction vessel and polystyrene microparticles. It is reasonable to assume that low NSB will be favorable to assay precision, by improving the signal-to-noise ratio.

TABLE 3

|  | ng/mL CsA | Triton ® X-100 | Triton ® X-114 | Igepal CA-520 | Triton ® SP-135 | Tetronic 1107 | Brij 700 |
|---|---|---|---|---|---|---|---|
| CAL A | 0 | 736,795 | 637,497 | 688,088 | 480,075 | 694,375 | 351,879 |
| CAL B | 40 | 440,071 | 415,282 | 476,408 | 340,997 | 519,584 | 268,978 |
| CAL C | 150 | 251,156 | 257,303 | 321,951 | 210,246 | 401,285 | 216,236 |
| CAL D | 400 | 145,546 | 149,332 | 215,980 | 129,438 | 296,499 | 173,188 |
| CAL E | 800 | 96,478 | 105,218 | 148,882 | 95,797 | 238,658 | 150,633 |
| CAL F | 1500 | 70,707 | 74,121 | 106,614 | 78,521 | 203,810 | 137,096 |
|  | % CV | 5.7 | 7.7 | 6.5 | 9.8 | 12.6 | 29.6 |
|  | B/A | 0.60 | 0.65 | 0.69 | 0.71 | 0.75 | 0.76 |
|  | F/A | 0.10 | 0.12 | 0.15 | 0.16 | 0.29 | 0.39 |

As can be seen from Table 3, the detergents are listed in order of increasing B/A and F/A ratio (indicative of increasing NSB). There is a distinct trend in imprecision as these ratios increase. Also, two of the detergents, Triton® SP-135 and Brij 700, cause a significant reduction in Cal A assay signal. Tetronic 1107 and Brij 700 had the highest F/A. A lower amount of Triton® X-100 was found to provide the best precision and the lowest B/A and F/A. Accordingly, all experiments performed in the following examples used TX100 as the Tracer detergent.

Example 3

The Effect of Reduced Triton® X-100 on Assay Performance

Figure 5:
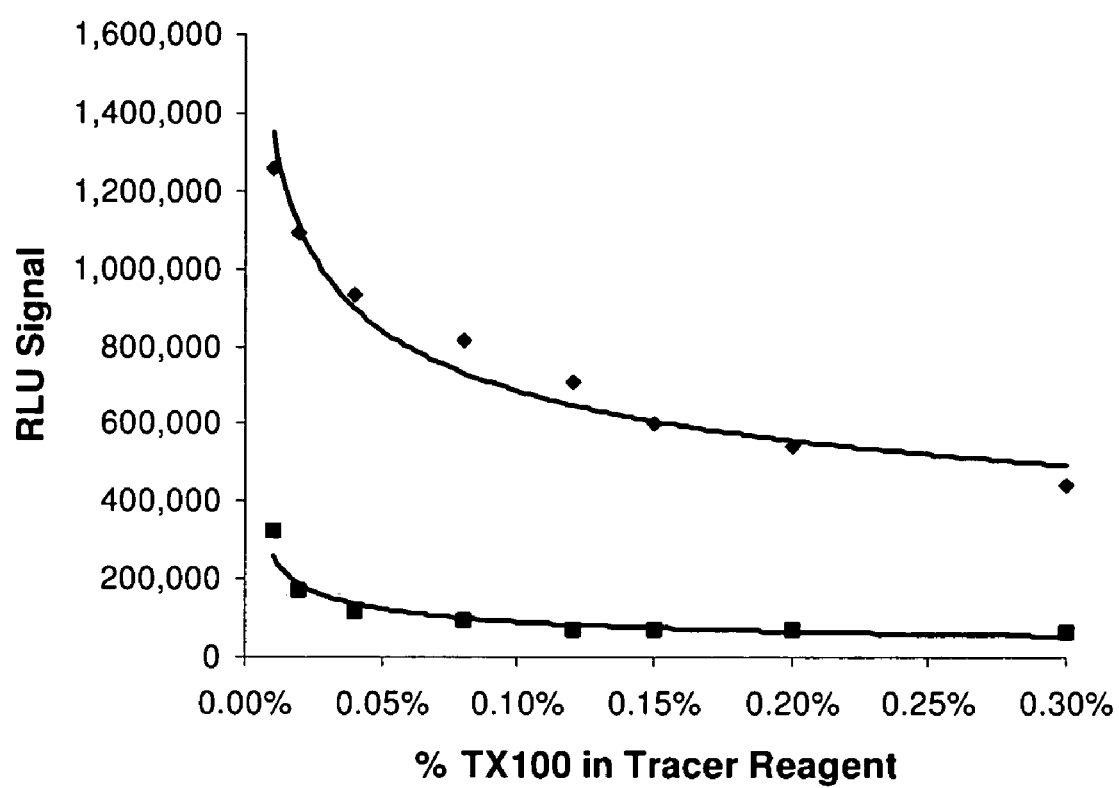
FIG. 5 is a graph of the effect of tracer Triton® X-100 concentration on relative light unit (RLU) signal as described in Example 3. Abscissa: % Triton® X-100 ("TX100") in tracer. Ordinate: RLU signal. Symbols: diamonds, Calibrator A (0 ng/mL CsA); squares, Calibrator F (1500 ng/mL CsA).
Figure 6:
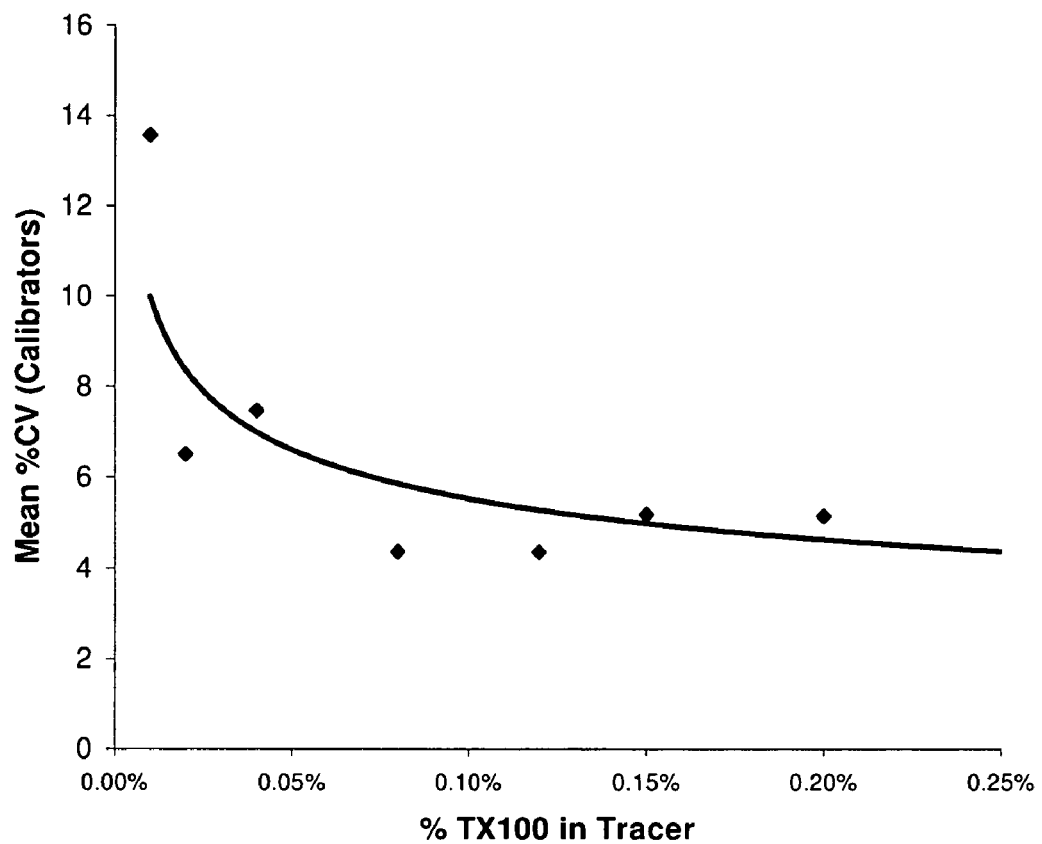
FIG. 6 is a graph of the effect of tracer TX100 concentration on % Concentration CVs as described in Example 3. Abscissa: % TX100 in tracer. Ordinate: Mean % CV. Symbols: Data points obtained for Series 1 Calibrators (Calibrator A containing 0 ng/mL CsA).

This example demonstrates how detergent concentration affects performance, using the preferred detergent (TX100). The assays were performed as in Example 1, Format 4 (Delayed Tracer addition in the 2-Step Assay format). The data show a strong effect on both RLU signal and precision and are depicted in Table 4, and graphically in FIGS. 5 and 6.

As can be seen from Table 4, TX100 reduces RLU signal and assay % CV dramatically in the 0.01% to 0.12% range. At higher ranges the effect flattens out (see, FIGS. 5 and 6). Accordingly, all experiments performed in the following examples used a concentration of 0.12% TX100.

Example 4

The Effect of Different Detergent Composition in the Extraction Step

This example illustrates that modifications to the detergent present in the whole blood pretreatment step (referred to as the extraction, yielding the blood extract) can have marked effects on the shape of the calibration curve.

For these experiments, three different pretreatment methods were employed based on the blood pretreatment steps used in assays for three different instruments of Abbott Laboratories (Abbott Park, Ill.): (1) the ARCHITECT® ("ARCH") as described above; (2) the TDx ("TDx"), a system that uses fluorescence polarization immunoassay (FPIA) to measure serum drug concentration in a patient; and (3) AxSYM® or AxSYM® Plus (collectively referred to as "AXS"), having three separate analytical technologies for processing immunoassays, i.e., microparticle enzyme immunoassay, FPIA, and ion-capture immunoassay.

The component composition before and after extraction using the three pretreatment methods is shown below in Table 5.

TABLE 4

|  | ng/mL CsA | 0.01% | 0.02% | 0.04% | 0.08% | 0.12% | 0.15% | 0.20% | 0.30% |
|---|---|---|---|---|---|---|---|---|---|
| CAL A | 0 | 1,258,564 | 1,094,498 | 930,200 | 816,422 | 707,907 | 599,404 | 542,550 | 445,513 |
| CAL B | 40 | 845,584 | 686,082 | 572,351 | 509,191 | 425,507 | 372,974 | 365,371 | 314,560 |
| CAL C | 150 | 596,919 | 432,876 | 339,755 | 315,198 | 256,571 | 231,313 | 226,640 | 222,492 |
| CAL D | 400 | 430,981 | 286,878 | 210,908 | 189,764 | 160,982 | 159,249 | 156,030 | 145,701 |
| CAL E | 800 | 368,695 | 217,101 | 151,063 | 129,044 | 103,839 | 107,922 | 103,559 | 100,450 |
| CAL F | 1500 | 322,522 | 172,874 | 117,797 | 91,954 | 73,614 | 72,903 | 70,136 | 66,961 |
|  | % CVs | 13.6 | 6.5 | 7.5 | 4.4 | 4.4 | 5.2 | 5.1 | 5.2 |
|  | B/A | 0.67 | 0.63 | 0.62 | 0.62 | 0.60 | 0.62 | 0.67 | 0.71 |
|  | F/A | 0.26 | 0.16 | 0.13 | 0.11 | 0.10 | 0.12 | 0.13 | 0.15 |

TABLE 5

| Sample | Reagent & Sample Composition | | | Extracted Sample Composition | | |
|---|---|---|---|---|---|---|
| Pretreatment | TDx | ARCH | AXS | TDx | ARCH | AXS |
| Volume Ratios | | | | | | |
| (B/S/P) | 150/50/300 | 200/100/400 | 150/50/300 | NQ[1] | NQ[1] | NQ[1] |
| Blood Sample | | | | | | |
| Cal F, ng/mL | 1500 | 1500 | 800 | 450 | 429 | 240 |
| % CsA | 100% | 100% | 100% | 30% | 29% | 30% |
| Solubilization | | | | | | |
| % Saponin | 2.0 | 1.0 | 0.2 | 0.20 | 0.14 | 0.02 |
| % Tergitol | 1.9 | None | 0.2 | 0.19 | None | 0.02 |
| Precipitation | | | | | | |
| % Methanol | 50 | 70 | 90 | 30 | 40 | 54 |
| % Ethylene Glycol | 30 | 20 | 10 | 18 | 11 | 6 |
| mm Zinc Sulfate | 60 | 50 | 60 | 36 | 29 | 36 |

[1]The designation "NQ" indicates this was not quantitated.

The three pretreatment methods are quite similar in composition, but vary in % methanol and ethylene glycol in the extracted sample. In Table 5, methanol increases going from TDx to ARCHITECT® to AxSYM®, but ethylene glycol decreases. In addition, TDx and AxSYM® solubilization reagents contain Tergitol, which is not present in the ARCHITECT® pretreatment step.

These three extraction methods were used independently on three sets of CsA calibrators, and the resulting extracts were all run on the ARCHITECT® analyzer. The effect of the pretreatment reagent on the ARCHITECT® CsA was assessed in terms of RLU signals, curve ratios and mean % CVs, with results shown below in Table 6 and depicted graphically in FIG. 7.

TABLE 6

| | RLUs | | |
|---|---|---|---|
| CsA ng/mL | TDx | ARCH | AXS |
| 0 | 908,888 | 913,203 | 871,849 |
| 40 | 858,303 | 588,619 | 742,037 |
| 150 | 759,988 | 349,284 | 600,800 |
| 400 | 650,811 | 211,024 | 469,253 |
| 800 | 566,833 | 142,161 | 418,226 |
| 1,500 | 497,804 | 103,395 | 309,611 |
| % CV | 5.4 | 4.3 | 7.8 |
| B/A | 0.94 | 0.64 | 0.85 |
| F/A | 0.55 | 0.11 | 0.36 |

Figure 7:
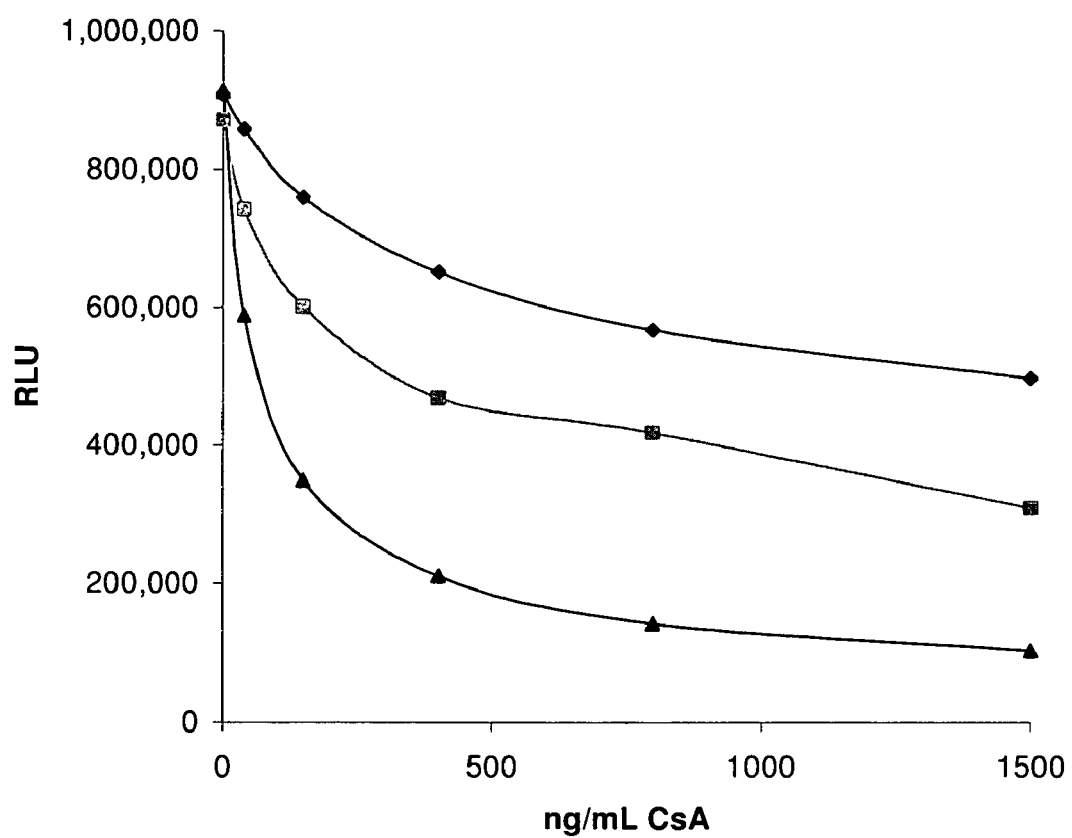
FIG. 7 is a graph showing the effect of the extraction method on curve shape, as described in Example 4. Abscissa: CsA concentration in ng/mL. Ordinate: RLU signal. Symbols: diamonds, assay results using ARCHITECT® pretreatment; squares, assay results using AxSYM® pretreatment; circles, assay results using TDx pretreatment.

As can be seen in FIG. 7, the curve with the worst curve shape is that resulting from the TDx pretreatment condition, with the AxSYM® pretreatment condition being intermediate between that of the TDx and ARCHITECT®. This progression does not correlate with organic solvent or saponin concentration, nor with the amount of CsA transferred to the reaction, which is 29% to 30% of the total blood CsA (see Table 5). However, this observation does correlate with the amount of Tergitol present in the Solubilization reagent employed in the pretreatment step. Tergitol seems unlikely to increase NSB and raise the CsA calibrator (in this case Calibrator F having 1500 ng/mL CsA) RLU signal, since the precision does not change nearly as dramatically as examples of other detergents in Table 3. Tergitol should have no effect on the Tracer incubation step, since saponin and Tergitol are both removed by the wash step before Tracer-TX100 reagent is added.

A final possibility seems more likely, namely that Tergitol is non-specifically binding CsA more strongly than saponin. Since CsA is highly water insoluble molecule, it is reasonable to propose that it would be preferentially sequestered in the hydrophobic interior of detergent micelles rather than in the bulk aqueous solvent. Moreover, since antibody is in equilibrium with free CsA, not total CsA in the binding step, the % of total CsA bound to antibody at equilibrium will be reduced if the binding equilibrium with detergent lowers the free CsA. This will not be a quantitative problem if Tracer and CsA are present together and are bound in similar proportion by detergent. This is the situation described in three of the assay formats outlined in Table 1, namely assay Formats 1-3. By contrast, in the fourth example (i.e., assay Format 4 having the low metabolite cross-reactivity), the CsA and Tracer binding steps occur in very different detergent environments.

Example 5

Replication of Curve Shape Change Using Another Detergent

This example illustrates that the Tergitol effect is not detergent-specific or related to differential extraction from blood.

In this example, extraction was performed with saponin detergent only. Triton® X-100 was added to the Assay Diluent, to introduce TX100 during the first antibody binding step, but not during the extraction. Calibration curves were compared with and without 0.05% TX100 in the Assay Diluent reagent. Results of the studies are shown in FIG. 8.

Figure 8:
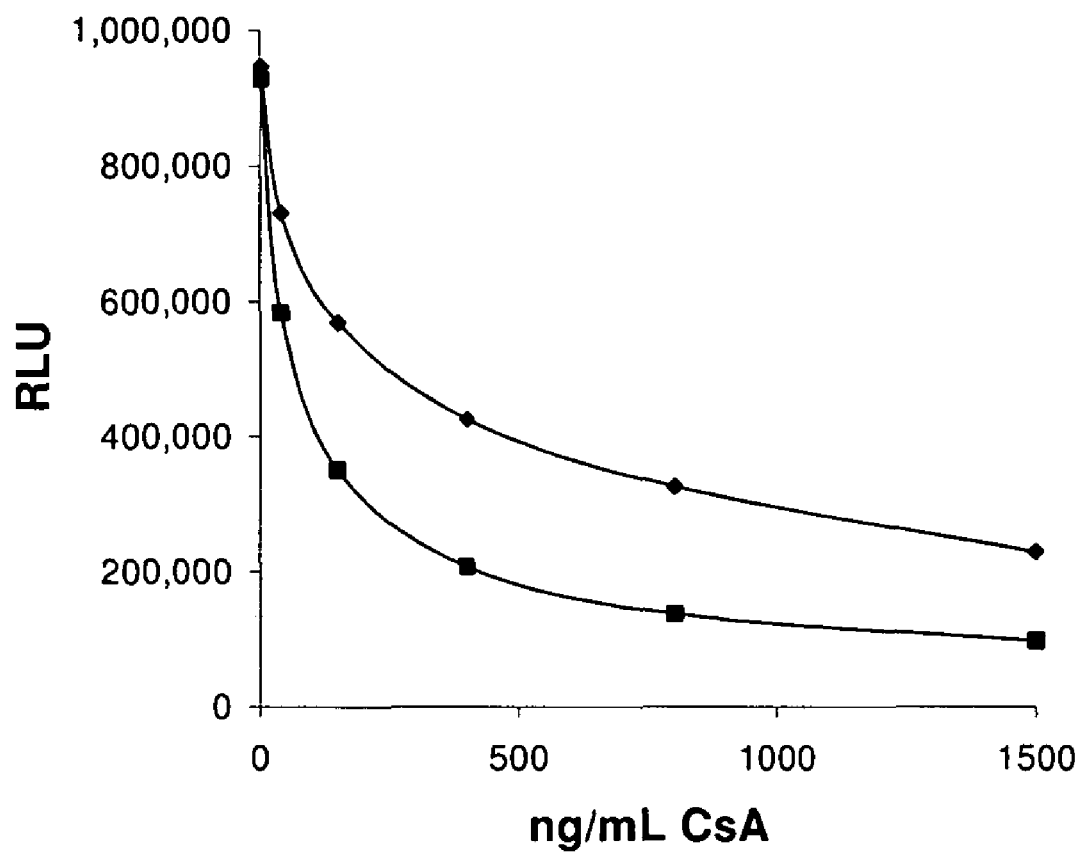
FIG. 8 is a graph showing the effect of addition of TX100 to assay diluent, as described in Example 5. Abscissa: CsA concentration in ng/mL. Ordinate: RLU signal. Symbols: squares, TX100 added; diamonds, no TX100 added.

As can be seen from FIG. 8, the addition of TX100 shifted the calibration curve upward without significantly changing the precision (i.e., the CV without TX100 was 5.4%, whereas with TX100 was 6.8%). This observation is consistent with additional binding of CsA by TX100 occurring during the first assay incubation, thus reducing the amount of free CsA available to bind to Antibody. The findings confirm that this is not related to the extraction step, which was done with saponin only.

Example 6

Rationale For Achieving Low Metabolite Cross-Reactivity

This example demonstrates the relative concentrations of assay components and estimates some of the binding equilibria that determine cross-reactivity.

A listing of active ingredients in the first and second steps of the low cross-reactivity assay is set forth in Table 7 below.

TABLE 7

|  | First Step | Second Step |
|---|---|---|
| Reaction volume | 215 μL | 50 μL |
| Component | Concentrations | |
| Methanol | 14% | None |
| Saponin | 3 mM | None |
| mAb binding sites | 0.2 nM | 1 nM |
| 200 ng/mL CsA | 17 nM | ~0.5 nM |
| 1000 ng/mL Metabolite | 83 nM | ~2.5 nM |
| CsA-Acr Tracer | None | 0.5 nM |
| TX-100 | None | 2 mM |
| Detergent/CsA Ratio | ~200,000 | ~2,000,000 |
| Antibody/CsA Ratio | 0.01 | ~2 |

It can be seen from Table 7 that there is a huge excess of detergent over CsA in both steps. This would allow detergents micelles to sequester hydrophobic small molecules (CsA, Metabolite, Tracer) and keep them in solution during the antibody binding and competition reactions. In the first step, only about 1% of the CsA can be bound by the small amount of antibody present. This suggests that the antibody is in equilibrium with the small fraction of CsA not bound by detergent, and that about 99% of the CsA is removed in the first wash step. This allows a much smaller amount of CsA to participate in the Tracer competition step. This low CsA concentration is now close to its equilibrium dissociation constant ($K_D$) with antibody. The $K_D$ has not been measured directly, but has been estimated to be about 0.5 nM by measuring the binding of a CsA-Fluorescein Tracer. For these experiments it is assumed that the Tracer $K_D$ is within an order of magnitude of the CsA $K_D$. The $K_D$ for metabolite is not known exactly, but since calculated metabolite % cross-reactivity is only in the range of about 7-20%, the metabolite $K_D$ must be larger by orders of magnitude. Without knowing all the binding constants for CsA, Metabolite, and tracer to their binding partners, it is not possible to come up with exact solutions for the binding equilibria, but estimates can be made. Such estimates are set forth in Table 8.

TABLE 8

|  | Conc. | $K_D$ | % Bound |
|---|---|---|---|
| First Incubation Step | | | |
| Metabolite | 83 nM | 750 nM | 10% |
| Cyclosporine | 17 nM | 0.5 nM | 97% |
| Ratio | 5 | 1500 | ~10% |
| Second Incubation Step | | | |
| Metabolite | 2.5 nM | 500 nM | 0.3% |
| CsA | 0.5 nM | 0.5 nM | 50% |
| Ratio | 5 | 1500 | 0.6% |

For studies in this example, it has been assumed that metabolite concentration is 1000 ng/mL, a 5-fold concentration excess over CsA. It also has been assumed that the $K_D$ for Metabolite is 1500 times larger than the $K_D$ for CsA. The % bound calculation in Table 8 represents the fraction of Metabolite or CsA that would be bound under equilibrium conditions with an excess of antibody. In the assay situation, the antibody is, of course, much lower, and the relative binding of Metabolite and CsA can only be estimated as the ratio of % bound numbers. Due to the large differences in $K_D$ and the CsA and Metabolite concentrations in the first and second steps, the relative binding of Metabolite/CsA drops from approximately 10% to less than 1%. If this differential binding were measured by competition with labeled Tracer, one should see a large difference in metabolite cross-reactivity. In fact, Tracer competition in three of the four assay format examples described in Table 1 (i.e., Formats 1-3) occur under conditions of high CsA and Metabolite concentration relative to Tracer and antibody. These three assay formats also show significant metabolite cross-reactivity, depending on which assay components are added, and. in what order. The only assay format in which the Tracer reaction occurs at low CsA, metabolite and antibody concentrations is the one with low cross-reactivity (i.e., Format 4). This and the preceding examples thus provide a rationale for explaining the low cross-reactivity of assay Format 4.

Example 7

Cross-Reactivity Comparisons

This example demonstrates a cross-reactivity comparison of the ARCHITECT® CsA immunoassay set forth herein with other commercial assays.

In the presence of 300 ng/mL parent CsA, cross-reactivities for AM1 (at 1000 ng/mL) were 7% for AxSYM®, 4% for CEDIA, and essentially none for EMIT. Cross-reactivities for AM9 (500 ng/mL) were 12.6% for AxSYM®, 25% for CEDIA, and 6% for EMIT. Comparison with HPLC showed in heart and kidney recipients an average overestimation with the EMIT and the CEDIA of ~22%, and overestimation with AxSYM® of 32%. In liver recipients, the most challenging patient group, the CEDIA and the AxSYM® CsA assays showed a mean overestimation of 43% and 47%, respectively, and the EMIT differed by 31% compared with HPLC (see, Schütz et al., Cyclosporin whole blood immunoassays (Ax-SYM®, CEDIA, and EMIT): a critical overview of performance characteristics and comparison with HPLC. *Clinical Chemistry* 44:2158-2164 (1998)).

Dade RxLFlex cross-reactivity was measured in the presence of 200 ng/mL cyclosporine and was found to be 2-5% for AM1 (1000 ng/mL), 2% for AM9 (1000 ng/mL), 3-6% for AM4n (1000 ng/mL), 2-3% for AM19 (1000 ng/mL), and 1-2% for AM1c (1000 ng/mL).

Abbott ARCHITECT® cross-reactivity was measured in the presence of 200 ng/mL cyclosporine and was found to be −0.23% for AM1 (1000 ng/mL), 0.28% for AM9 (1000 ng/mL), 0.26% for AM4n (1000 ng/mL), —0.43% for AM19 (1000 ng/mL), and 0.41% for AM1c (1000 ng/mL).

Abbott TDx cross-reactivity was measured in the presence of 200 ng/mL cyclosporine and was found to be 6.7% for 500 ng/mL AM1, 19.4% for 250 ng/mL AM9, and not statistically significant for 250 ng/mL AM4n, for 250 ng/mL AM19, and for 250 ng/mL AM1c.

Abbott AxSYM® cross-reactivity was measured in the presence of 200 ng/mL cyclosporine and was found to be 6.9% for 500 ng/mL AM1, 10.8% for 250 ng/mL AM9, and not statistically significant for 250 ng/mL AM4n, for 250 ng/mL AM19, and for 250 ng/mL AM1c.

EMIT cross-reactivity with the four major CsA metabolites was evaluated in the presence of 200 ng/mL CsA. Of these metabolites, only M1 (AM9) showed significant cross-reactivity at 7%.

Example 8

Specificity Comparisons

This example demonstrates a specificity comparison of the ARCHITECT® CsA immunoassay set forth herein with other commercial assays.

The specificity of monoclonal immunoassays for CsA was addressed in the past mostly by direct comparison with HPLC or by measurement of purified metabolites. The ARCHITECT® CsA immunoassay described herein has been designed to give low cross-reactivity to CsA metabolites AM1 and AM9. Low cross-reactivity was confirmed using Dr. Holt's proficiency transplant patient pools and spiked versus HPLC results.

The ARCHITECT® CsA assay showed a <10% bias versus the HPLC results, whereas the TDx CsA assay showed a 34.23% positive bias versus HPLC, and the AxSYM® CsA assay showed a 17.77% positive bias versus HPLC. This appears to be due to the fact that TDx and AxSYM® CsA assays are cross-reactive to AM1 and AM9 and show variable positive concentration biases mainly in the CsA trough region (<500 ng/mL) whereas the ARCHITECT® CsA assay shows <1% cross-reactivity for all Cyclosporine metabolites.

Analysis of these three assays using Dr. Holt's proficiency spiked patient pools versus HPLC, showed all three assays (ARCHITECT®, TDx, and AxSYM®) to be within a +/−5% bias due to the fact that the spiked samples do not have any Cyclosporine metabolites present.

One skilled in the art would readily appreciate that the present disclosure is well adapted to carry out the objects and obtain the ends and advantages mentioned, as well as those inherent therein. The compositions, formulations, methods, procedures, treatments, molecules, specific compounds described herein are presently representative of preferred embodiments, are exemplary, and are not intended as limitations on the scope of the disclosure. It will be readily apparent to one skilled in the art that varying substitutions and modifications may be made to the disclosure disclosed herein without departing from the scope and spirit of the disclosure.

All patents and publications mentioned in the specification are indicative of the levels of those skilled in the art to which the disclosure pertains. All patents and publications are herein incorporated by reference to the same extent as if each individual publication was specifically and individually indicated to be incorporated by reference.

The disclosure illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An immunoassay for assessing the amount of an analyte of interest in a test sample, wherein the analyte is a hydrophobic drug that metabolizes to form one or more cross-reacting metabolites, the immunoassay comprising the steps of:
    (a) contacting the test sample with one or more pretreatment reagents to form a first mixture, wherein the one or more pretreatment reagents lyse any cells and solubilize any analyte and cross-reacting metabolites present in the test sample;
    (b) contacting the first mixture with an antibody specific for the analyte to form a second mixture comprising a complex of the antibody with either analyte or metabolite, wherein the amount of antibody with which the first mixture is contacted is from about 0.1% to about 10% of the amount of analyte in the test sample;
    (c) washing the second mixture to remove any analyte and any metabolite not complexed with the antibody and to form a third mixture in which the analyte concentration is decreased to near the equilibrium dissociation constant ($K_D$) of the antibody for analyte wherein the analyte and metabolite concentrations are decreased in the third mixture from about 10-fold to about 500-fold as compared to in the test sample;
    (d) contacting the third mixture with a specific binding partner of the antibody labeled with a detectable label ("tracer") to form a fourth mixture comprising a complex of the antibody with tracer ("antibody-tracer complex");
    (e) washing the fourth mixture to remove any tracer not complexed with antibody; and
    (f) detecting the antibody-tracer complex as measure of the amount of analyte present in the test sample, wherein the immunoassay has less than about 10% cross-reactivity with any one or more cross-reacting metabolites present in the sample.

2. The immunoassay of claim 1, wherein the immunoassay has less than about 5% cross-reactivity with any one or more cross-reacting metabolites present in the sample.

3. The immunoassay of claim 1, wherein the antibody specific for the analyte is immobilized on a solid phase.

4. The immunoassay of claim 1, wherein the one or more pretreatment reagents precipitate in step (a) any analyte binding protein present in the sample.

5. The immunoassay of claim 4, which further comprises removing any analyte binding protein from the first mixture.

6. The immunoassay of claim 1, wherein in step (d) the amount of analyte present in a complex with antibody ranges from about 1.0 and about 10.0 nM, and the tracer is present in an amount from between about 0.1 to about 1.0 nM.

7. The immunoassay of claim 1, wherein the test sample is whole blood.

8. The immunoassay of claim 1, wherein the hydrophobic drug is soluble in detergent or organic solvent.

9. The immunoassay of claim 1, wherein the hydrophobic drug is an immunosuppressive.

10. The immunoassay of claim 9, wherein the immunosuppressive is selected from the group consisting of tacrolimus, sirolimus and cyclosporine.

11. The immunoassay of claim 10, wherein
    (a) the immunosuppressive is tacrolimus and the metabolite is selected from the group consisting of M-I, M-II, M-III, and combinations thereof;
    (b) the immunosuppressive is cyclosporine and the metabolite is selected from the group consisting of M1, M8, M9, M13, M17, M18, M21 and combinations thereof; or
    (c) the immunosuppressive is sirolimus and the metabolite is selected from the group consisting of 11-Hydroxy-sirolimus, 41-O-demethyl-sirolimus, 7-O-demethyl-sirolimus, 41-O-demethyl-hydroxy-sirolimus and combinations thereof.

12. The immunoassay of claim 9, wherein the immunosuppressive is cyclosporine and the metabolites are AM1 and AM9.

13. The immunoassay of claim 1, wherein the antibody is selected from the group consisting of a polyclonal antibody, a monoclonal antibody, a humanized antibody, a F(ab)'2, a chimeric antibody, a human antibody, and an affinity maturated antibody.

14. The immunoassay of claim 1, wherein the solid phase is selected from the group consisting of a magnetic particle, bead, test tube, microtiter plate, cuvette, membrane, a scaffolding molecule, film, filter paper, disc, and chip.

15. The immunoassay of claim 1, wherein the detectable label is selected from the group consisting of a radioactive label, an enzymatic label, a chemiluminescent label, a fluorescent label, a thermometric label, and an immunopolymerase chain reaction label.

16. The immunoassay of claim 1, wherein the tracer comprises multiple binding partners.

17. The immunoassay of claim 1, wherein the one or more pretreatment reagents comprise saponin, methanol, ethylene glycol, and zinc sulfate.

18. The immunoassay of claim 1, wherein the second mixture further comprises an assay diluent.

19. The immunoassay of claim 18, wherein the assay diluent comprises a buffer, salt, detergent, solvent, or combinations thereof.

20. The immunoassay of claim 1, wherein the fourth mixture in step (d) further comprises a detergent.

21. The immunoassay of claim 20, wherein the detergent is reduced Triton® X-100.

22. The immunoassay of claim 1, wherein the analyte is cyclosporine and the tracer comprises cyclosporine labeled with acridinium.

23. The immunoassay of claim 1, wherein the antibody in step (b) has a $K_D$ for cross-reacting metabolite that is between about 10-fold and about 1000-fold higher than for analyte.

24. The immunoassay of claim 1, wherein the immunoassay relates an amount of the antibody-tracer complex formed to the amount of the analyte in the test sample either by use of a standard curve for the analyte, or by comparison to a reference standard.

25. The immunoassay of claim 1, further comprising:
(i) incubating the first mixture in step (a) for a first incubation period;
(ii) incubating the second mixture in step (b) for a second incubation period; and
(iii) incubating the fourth mixture in step (d) for a third incubation period.

26. The immunoassay of claim 25, wherein the first incubation period comprises a period of from about 2 minutes to about 60 minutes.

27. The immunoassay of claim 25, wherein the second incubation period comprises a period of from about 2 minutes to about 30 minutes.

28. The immunoassay of claim 25, wherein the third incubation period comprises a period of from about 2 minutes to about 30 minutes.

* * * * *